United States Patent [19]
Zdeb

[11] Patent Number: 5,205,823
[45] Date of Patent: Apr. 27, 1993

[54] RETRACTABLE SYRINGE

[75] Inventor: Brian Zdeb, Round Lake Park, Ill.

[73] Assignee: Retrax, Inc., Tomball, Tex.

[21] Appl. No.: 771,762

[22] Filed: Oct. 4, 1991

Related U.S. Application Data

[63] Continuation-in-part of Ser. No. 592,623, Oct. 4, 1990, Pat. No. 5,112,315.

[51] Int. Cl.$^5$ .............................................. A61M 5/00
[52] U.S. Cl. .................................... 604/110; 604/195
[58] Field of Search ............... 604/195, 110, 187, 218, 604/263, 192

[56] References Cited

U.S. PATENT DOCUMENTS

| | | | |
|---|---|---|---|
| 4,944,723 | 7/1990 | Haber et al. | 604/110 |
| 4,978,340 | 12/1990 | Terrill et al. | 604/195 |
| 5,030,208 | 7/1991 | Novacek et al. | 604/110 X |

Primary Examiner—John D. Yasko
Attorney, Agent, or Firm—David M. Ostfeld

[57] ABSTRACT

A retractable syringe includes a barrel [12, 212], one end of which comprises a mounting collar [14, 214]. A needle carrier [16, 216] is releasably mounted within the collar [14, 214], and releasably supports a needle cartridge [18, 218]. A hypodermic needle [20] is mounted within the cartridge [18, 218]. A sheath [22, 222, 418, 420, 422] attaches at one end to the cartridge, and at the other end to the collar. A plunger [36, 236] is telescoped into the barrel [12, 218], and includes a relatively hard piston sealingly engaging the barrel [12, 218]. The piston includes a latch [38, 238] for engaging the carrier [16, 216] and releasing it from the collar [14, 214]. A pocket [76, 476] in the carrier has a support member [54] in its center, and a pair of helical ribs [64] for threadingly engaging a pair of tabs on the cartridge [18, 218]. The cartridge [18, 218] sealingly receives the support member [54]. The collar [14, 214] has slots [82] and inclined threads [84, 256] in its bore wall for engaging lugs [48, 248] on the carrier. The inclined threads [84, 256] have a friction bump [86, 270] near their blind ends. A retaining pin [92, 94] prevents relative rotation between the carrier [16, 216] and collar [14, 214] prior to desired retraction of the needle [20] into the barrel [12, 212]. Alternative embodiments include a barrel which may be resilient or non-resilient and a hard or soft resilient piston, respectively, having a plunger head secured therewithin and attached to the plunger. A latch is attached to the plunger head, and is received in a recess in the carrier to engage latch stops for rotating the carrier to release it from the collar. Alternative embodiments may include means for securing the plunger in the barrel after retraction.

8 Claims, 17 Drawing Sheets

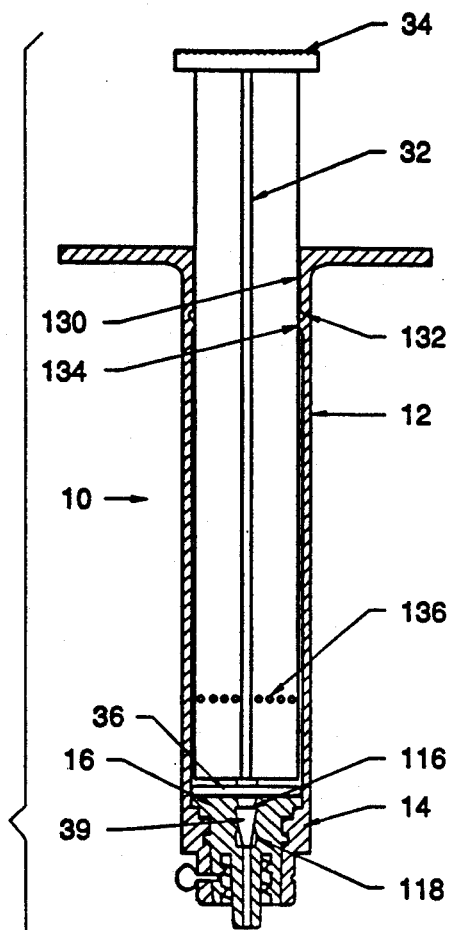
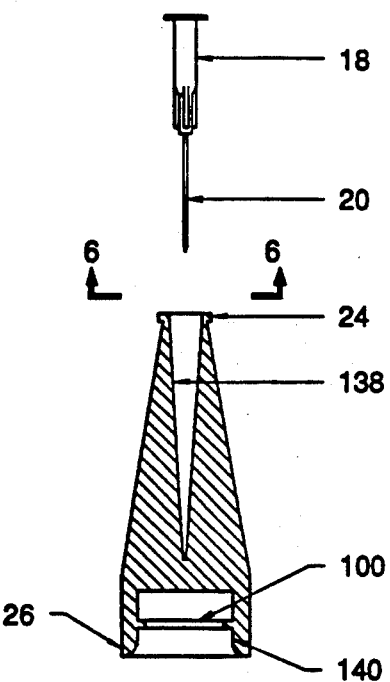
FIG.2
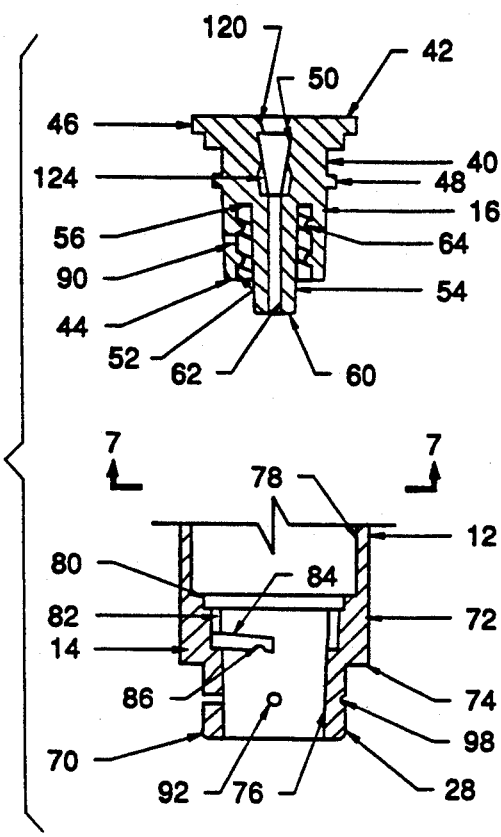
FIG.3
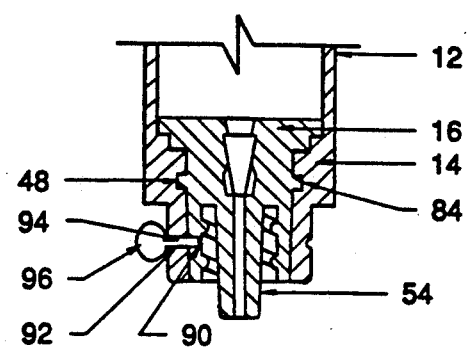
FIG.4

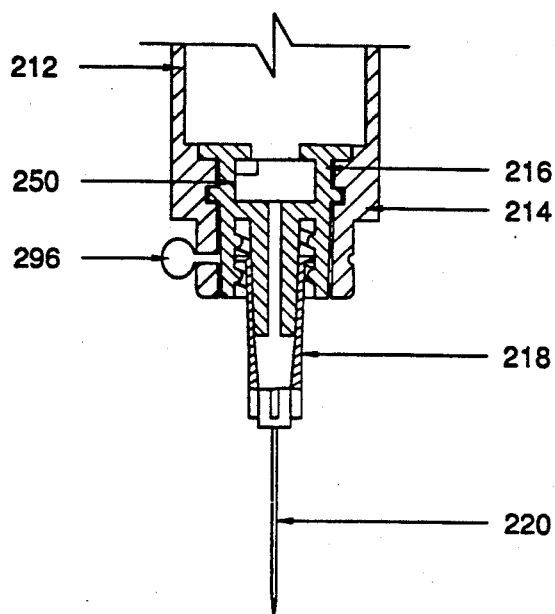
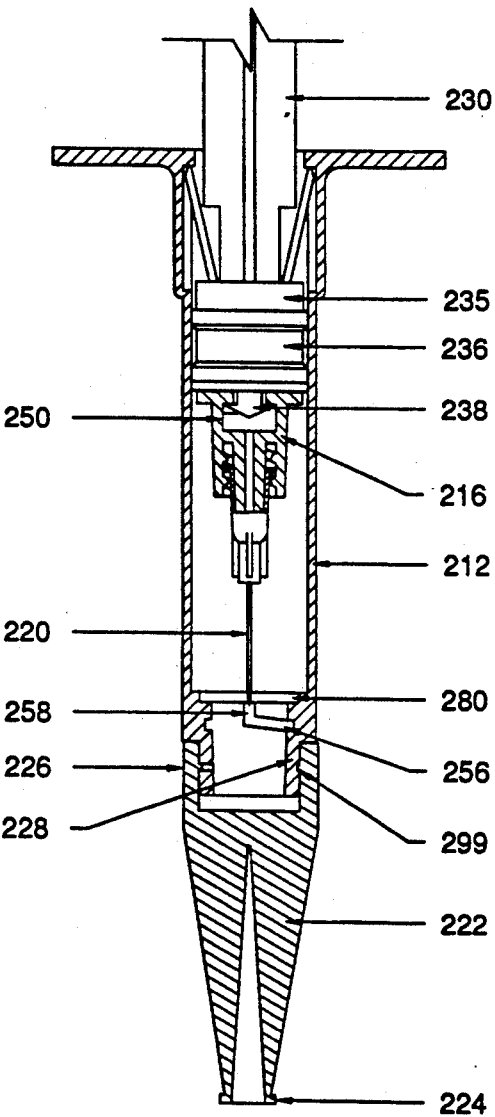
FIG.13
FIG.14

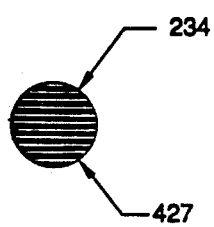 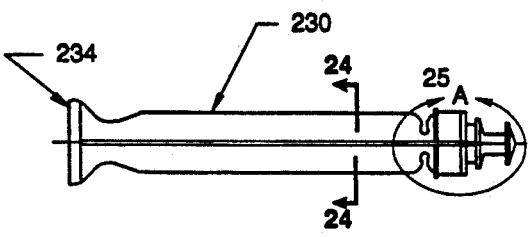 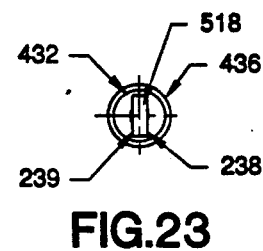
FIG.22  FIG.21  FIG.23
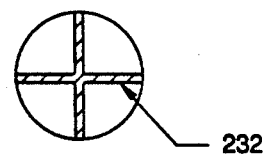
FIG.24
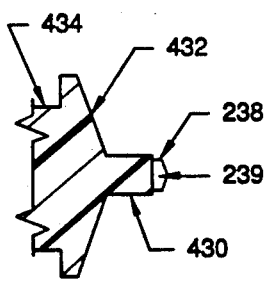 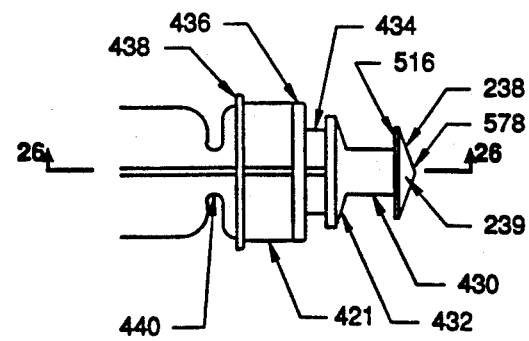
FIG.26  FIG.25

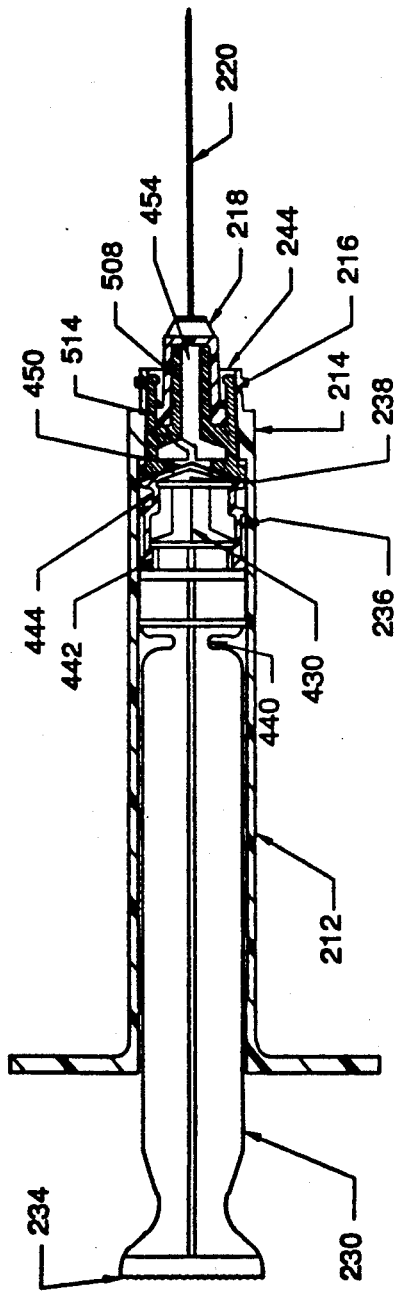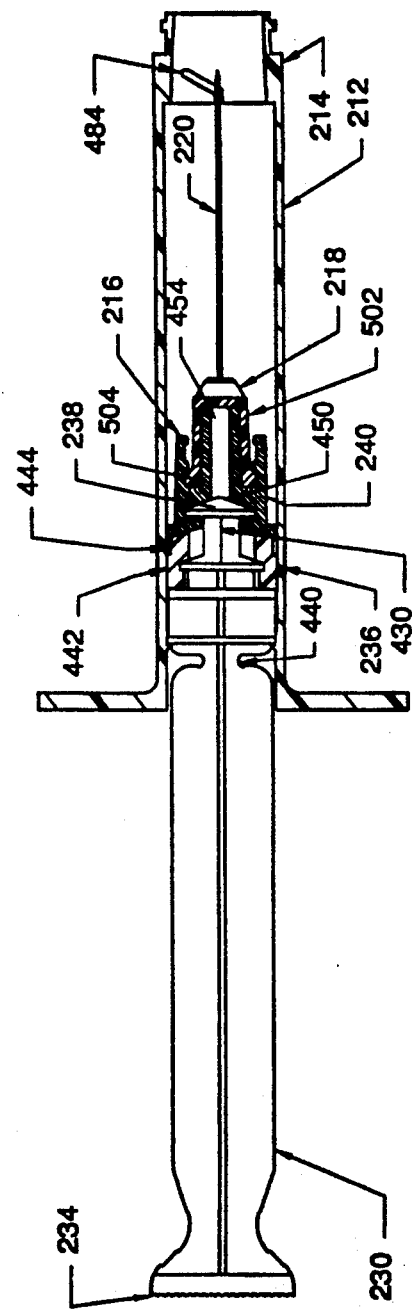

RETRACTABLE SYRINGE

CROSS-REFERENCE TO RELATED APPLICATION

This application is a continuation in part of U.S. application Ser. No. 592,623 filed Oct. 4, 1990, now U.S. Pat. No. 5,112,315 by Walter W. Gloyer and Frederick G. Bright, entitled "Improvements in Safety Disposable Syringe".

BACKGROUND OF THE INVENTION

The present invention relates generally to retractable hypodermic syringes, and more particularly to a retractable hypodermic syringe having a needle carrier adapted for releasably attaching a needle cartridge thereto prior to use. The present invention relates further to such a hypodermic syringe having means for retarding the unlatching of the needle carrier from the mounting collar of the syringe barrel during installation or removal of a needle cartridge, and still further to an invertible protective cover adapted at one end for sheathing the hypodermic needle prior to use, and at the other end for releasably attaching to and enclosing, or otherwise closing, a hub of the mounting collar at an end of the syringe barrel in the absence of a needle cartridge.

In the past, needle stick injuries suffered by medical personnel and others in the course of using hypodermic syringes have presented a serious problem. Serious diseases such as hepatitis and AIDS may be transmitted by needle stick injuries, resulting in the needless suffering, and possibly even in the death, of the unfortunate victims. Of late, the onslaught of AIDS has resulted in needle stick injuries posing an even greater health hazard because of the virtual certain death, at least insofar as research to date indicates, of the injured person if he or she contracts the disease.

In order to minimize the risk of needle stick injuries, retractable syringes have been developed which enable the retraction of the needle into the barrel of the syringe following use and prior to disposal. The movement of the needle in the retracted position is typically limited such that normally it will not again protrude from the barrel, and normally will not again come into contact with a health care worker or other person. Retraction and retention of the possibly contaminated needle into the barrel thus protectively isolates the needle and keeps it out of further human contact under normal circumstances. Such a retractable syringe is shown, for example, in U.S. Pat. No. 4,747,830, issued May 31, 1988, to Walter W. Gloyer and Frederick G. Bright, also the inventors herein, the disclosure of which is hereby incorporated by reference as if fully recited herein, including the references to and citations of the state of the art.

At times, persons having a need to use a hypodermic syringe will desire to select a particular size or shape of needle, such as one relatively longer or shorter than others he or she typically uses, or one having a larger or smaller diameter Hypodermic needle cartridges have been used in the past for nonretractable syringes. It would be advantageous if a health care worker or other such person could simply select a needle cartridge having a needle of the desired size and shape and easily install it in a commonly configured retractable syringe body. This would afford the syringe user the flexibility of meeting his or her particular medical needs with a variety of needles but only a single inventory of syringe bodies, as well as the safety and protection that a retractable syringe provides against needle stick injuries, while assuring reliability in connection. Since only one configuration of syringe body need be manufactured for use with a virtually unlimited selection of needle cartridges, the savings in tooling and manufacturing costs would also be significant. Moreover, the manufacture of a common syringe body without a needle permanently attached would simplify the manufacturing process for the retractable syringe, since the hypodermic needle would not have to be installed during manufacture of the syringe body.

One type of hypodermic needle cartridge used in the past is adapted for threaded engagement in a pocket disposed on the syringe barrel. The pocket typically has a needle cartridge support member disposed at or near its center, which is sealingly received in a correlatively shaped bore in the body of the needle cartridge. The body of the needle cartridge in one such prior art cartridge arrangement is provided with a pair of diametrically opposed tabs which threadedly engage a pair of axially spaced apart helical threads in the pocket on the syringe barrel.

A hypodermic syringe needle typically is provided with a protective sheath for covering the needle prior to use of the syringe. With conventional non-retractable syringes, the protective sheath may be reinstalled on the needle following use, but such reinstallation also involves the inherent risk of a needle stick injury from improper or careless handling or the like of the needle, the sheath, or both. Sometimes the person attempting to reinstall the sheath may not be physically able to do so easily, as might be the case, for example, if the person were to suffer from arthritis, a nerve disorder, or other problem. Moreover, U.S. Center for Disease Control guidelines now prohibit the recapping of syringes with the needle covers after use.

Following use of a retractable syringe, there is no need to reinstall the protective sheath, so the risk of a needle stick arising from such reinstallation is eliminated.

There is another potential disease-causing contamination problem, however, in that the syringe barrel is left open following retraction of the needle, thereby permitting any excess fluid or residue left in the syringe barrel to leak out into the environment. For example, if the excess fluid or residue were to be a contaminated fluid or residue, there is a risk of the contaminating virus or bacteria contaminating other medical tools or equipment in the area, possibly infecting persons who subsequently come into contact with such tools or equipment or the syringe. The needle sheaths typically used in the past for covering the needles are incapable of being used to enclose the barrels of retractable syringes following use and retraction of the needles into the barrels, so as to prevent such leakage and environmental contamination. Although sealable containers have been used in the past into which used syringes can be placed for disposal, such containers are typically completely separate items which must be provided along with the syringes or kept on hand somewhere close at hand. This results in extra labor and materials costs to manufacture such containers, extra shipping costs to supply them to the users, and extra storage and handling costs on-site.

It is an object of the present invention to provide a retractable syringe with a common barrel configuration which will reliably accept a needle cartridge in which is mounted a needle of virtually any desired size or shape. It is another object of the present invention to provide such a retractable syringe with a needle carrier releasably latched into a mounting collar of the barrel and into which the needle cartridge is installed, and means for preventing or retarding unlatching of the needle carrier from the mounting collar during installation or removal of the needle cartridge.

It is another object of the present invention to provide a retractable syringe on which a needle cartridge may be securely mounted such that the needle is firmly stabilized and supported in the needle carrier, and the needle carrier is securely latched in the mounting collar until such time as unlatching is desired.

It is another object of the present invention to provide a retractable syringe with a protective cover that will both cover the needle prior to use, and enclose the end of the barrel in which the needle cartridge is mounted either prior to installation of a needle cartridge in order to prevent contamination of the barrel, or following use of the syringe and retraction of the needle in order to prevent leakage of excess fluid or residue from the barrel.

It is another object of the present invention to provide such a syringe which is durable, reliable, and easy to use. It is still another object of the present invention to provide such a syringe which is inexpensive and simple to manufacture.

SUMMARY OF THE INVENTION

According to the preferred embodiment of the invention, a retractable syringe includes a barrel, one end of which comprises a needle carrier mounting collar. A needle carrier is releasably mounted within the mounting collar, and is adapted to releasably support therewithin a needle cartridge. A hypodermic needle is mounted within the needle cartridge. An invertible locking safety cover is adapted at one end to be frictionally retained on the needle cartridge, covering the needle, prior to use of the syringe, and at the other end to be positively locked to a hub of the mounting collar prior to installation of a needle cartridge into the needle carrier, and after use of the syringe and retraction of the needle into the barrel.

The needle carrier is sealingly mounted within the mounting collar from within the barrel. The needle cartridge is subsequently mounted to the proximal end of the needle carrier from outside the barrel.

A needle cartridge receiving pocket extends axially part way through the main body of the needle carrier from its proximal end. In the center of the pocket there is a needle cartridge support member having an axial bore in fluid communication with the interior of the needle carrier. The pocket has a pair of helical threads around its outer wall, forming a pair of lands which are a lure lock type thread upon which a pair of tabs disposed on the distal end of the needle cartridge ride in removing or installing the needle cartridge.

As with the other embodiments described below, the needle cartridge includes a main body having the tabs on its upper end adapted to be threadedly secured into the helically threaded pocket of the needle carrier. The cartridge has a central axial bore adapted to sealingly receive therewithin the needle cartridge support member of the needle carrier. A hypodermic needle of selected size and shape is mounted within the needle cartridge.

The mounting collar has a pair of axially extending slots in its bore wall traversed by the lugs on the needle carrier when it is installed into or removed from the mounting collar. The slots intersect and communicate with a pair of inclined threads in the bore wall of the mounting collar which extend part way around the bore wall. When the lugs on the needle carrier are inserted into the slots in the mounting collar and the needle carrier is then rotated in the appropriate direction, the lugs travel along the inclined threads into a position at the end of the inclined threads. Rotation of the needle carrier in the opposite direction passes the lugs along the inclined threads back to the slots for removal of the needle carrier from the mounting collar.

An elongate plunger is telescoped into and carried within the barrel. The plunger includes an injection piston attached at its proximal end, disposed within and sealingly engaging the barrel. The proximal face of the piston includes a stinger latch at or near its center.

The stinger latch is adapted to engage a seat in the recess of the needle carrier in such fashion that rotation of the stinger latch also rotates the needle carrier, and such that withdrawal of the stinger latch into the barrel also withdraws the needle carrier into the barrel. Rotation of the needle carrier until its lugs traverse the inclined threads and are in alignment with the axial slots permits withdrawal of the piston back into the barrel, along with the needle carrier, needle cartridge, and needle.

The mounting collar includes a groove around the periphery of its hub portion and adapted to receive an annular land disposed on the larger end of the locking safety cover in order to secure the cover to the hub, enclosing the barrel, when manufactured and prior to installation of a needle cartridge onto the syringe, and after retraction of the needle into the barrel.

The upper end of the barrel is provided with latching means for latching the plunger in retracted position and securing the needle safety within the barrel. The portion of the plunger protruding from the barrel may be broken off substantially flush with the end of the barrel. (The latching means for this embodiment and the alternative embodiment below may also be only the breaking off of the plunger in conjunction with the friction between the barrel and the piston, but depending on tolerances may not be reliable to hold the needle within the barrel.) The protective cover may then be installed on the mounting collar hub in order to enclose the barrel. The used syringe may then be safely discarded without further danger of a needle stick injury.

According to one alternative embodiment of the invention, a retractable syringe includes a resilient barrel, one end of which comprises a needle carrier mounting collar. A needle carrier is releasably mounted within the mounting collar, and is adapted to releasably support therewithin a needle cartridge. A hypodermic needle is mounted within the needle cartridge. An invertible locking safety cover is adapted at one end to be frictionally retained on the needle cartridge, covering the needle, prior to use of the syringe, and at the other end to be positively locked to a hub of the mounting collar prior to installation of a needle cartridge into the needle carrier, and after use of the syringe and retraction of the needle into the barrel.

The needle carrier is sealingly mounted within the mounting collar from within the barrel, and the needle cartridge is subsequently mounted to the proximal end of the needle carrier from outside the barrel. A plurality of radially outwardly extending bayonet lugs are disposed on the exterior of the needle carrier. A latch recess extends into the body of the needle carrier from its distal end for receiving the stinger latch.

A needle cartridge receiving pocket extends axially part way through the main body of the needle carrier from its proximal end. In the center of the pocket there is a needle cartridge support member having an axial bore in fluid communication with the latch recess. The pocket has a pair of helical ribs around its outer wall, forming a pair of lands upon which a pair of tabs disposed on the distal end of the needle cartridge ride in removing or installing the needle cartridge.

The needle cartridge includes a main body having the tabs on its upper end adapted to be threadedly secured into the helically threaded pocket of the needle carrier. The cartridge has a central axial bore adapted to sealingly receive therewithin the needle cartridge support member of the needle carrier. A hypodermic needle of selected size and shape is mounted within the needle cartridge.

The mounting collar has a pair of axially extending slots in its bore wall traversed by the lugs on the needle carrier when it is installed into or removed from the mounting collar. The slots intersect and communicate with a pair of inclined threads in the bore wall of the mounting collar which extend part way around the bore wall. The inclined threads each have a friction rise or bump on their proximal surfaces near their blind ends. When the lugs on the needle carrier are inserted into the slots in the mounting collar and the needle carrier is then rotated in the appropriate direction, the lugs travel along the inclined threads into a secure, seated position between the friction rises and the end walls of the inclined threads. Rotation of the needle carrier in the opposite direction passes the lugs over the friction rises and along the inclined threads back to the slots for removal of the needle carrier from the mounting collar.

A retaining pin may be disposed in aligned holes in the needle carrier and the mounting collar when they are fully assembled in order to prevent relative rotation between them prior to desired retraction of the needle into the barrel.

An elongate plunger is telescoped into and carried within the barrel. The plunger includes a relatively hard injection piston attached at its proximal end, disposed within and sealingly engaging the barrel. The proximal face of the piston includes a stinger latch at or near its center.

The stinger latch is adapted to engage a seat in the recess of the needle carrier in such fashion that upon removal of the retaining pin, rotation of the stinger latch also rotates the needle carrier, and such that withdrawal of the stinger latch into the barrel also withdraws the needle carrier into the barrel. Rotation of the needle carrier until its lugs traverse the inclined threads and are in alignment with the axial slots permits withdrawal of the piston back into the barrel, along with the needle carrier, needle cartridge, and needle.

The mounting collar includes a groove around the periphery of its hub portion and adapted to receive an annular land disposed on the larger end of the locking safety cover in order to secure the cover to the hub, enclosing the barrel, when manufactured and prior to installation of a needle cartridge onto the syringe, and after retraction of the needle into the barrel.

The upper end of the barrel is provided with latching means for latching the plunger in retracted position and securing the needle safely within the barrel. The portion of the plunger protruding from the barrel may be broken off substantially flush with the end of the barrel. (The latching means for this embodiment and the other embodiments may also be only the breaking off of the plunger in conjunction with the friction between the barrel and the piston, but depending on tolerances may not be reliable to hold the needle within the barrel.) The protective cover may then be installed on the mounting collar hub in order to enclose the barrel. The used syringe may then be safely discarded without further danger of a needle stick injury.

According to another alternative embodiment of the invention, an injection piston may be used with a non-flexible barrel. The injection piston comprises a soft resilient member having a plunger head secured therewithin and attached to the plunger. A latch member is attached to the proximal end of the plunger head, and is adapted to be received in a recess in the needle carrier and to engage latch stops in the recess for rotating the needle carrier to release it from the mounting collar.

A latching flange disposed on the upper end of the plunger head engages hooks disposed on flexible arms attached to the barrel when the plunger head is fully retracted into the barrel along with the needle carrier, needle cartridge, and needle, thereafter preventing movement of such members in a proximal direction and latching them in safe, secure position for disposal.

In the preferred and this alternative embodiment, the plunger latch may be covered by a thin resilient diaphragm, which preferably will follow the latch member.

Otherwise, the second alternative embodiment is substantially identical to the first alternative embodiment.

These and other objects and advantages of the invention will become apparent from the following description of the preferred embodiments when read in conjunction with reference to the following drawings.

BRIEF DESCRIPTION OF THE DRAWINGS

For a further understanding at the nature and objects of the present invention, in conjunction to this specification, reference should be had to the following drawings in which like parts are given like reference numerals and wherein:

FIG. 2 is a view partly in longitudinal section, partly exploded, and partly in elevation of the retractable syringe of FIG. 1, showing the needle cartridge separated from the needle carrier and the protective cover removed from the needle cartridge, and showing the plunger latch disposed in the recess in the upper end of the needle carrier.

FIG. 3 is a vertical sectional view of the mounting collar and needle carrier of the embodiment of FIG. 1 in exploded relation with the needle carrier in position to be inserted into the mounting collar FIG. 4 is a vertical sectional view of the assembled mounting collar and needle carrier of the embodiment of FIG. 1.

FIG. 13 is a vertical sectional view of the assembled mounting collar, needle carrier, and needle cartridge of the embodiment of FIG. 9.

FIG. 14 is, a vertical sectional view of the embodiment shown in FIG. 9, after use of the syringe and retraction of the needle cartridge and needle into the syringe barrel.

FIG. 21 is a side view of the preferred embodiment of the plunger of the retractable syringe of FIG. 15.

FIG. 22 is the distal end view of the plunger of FIG. 21.

FIG. 23 is the proximal end view of the plunger of FIG. 21.

FIG. 24 is a cross-sectional view of FIG. 21 taken along section lines 24—24 of FIG. 21.

FIG. 25 is a detail view of the proximal end of the plunger of FIG. 21.

FIG. 26 is a partial cross-sectional view of the proximal end of FIG. 25 taken along section lines 26—26 of FIG. 25.

FIG. 42 is a view in longitudinal section of the retractable syringe of FIG. 15, showing the assembly for normal operation.

FIG. 43 is a view in longitudinal section of the retractable syringe of FIG. 15, showing the assembly retracted.

DESCRIPTION OF THE PREFERRED EMBODIMENT AND ALTERNATE EMBODIMENTS OF THE INVENTION

Figure 1:
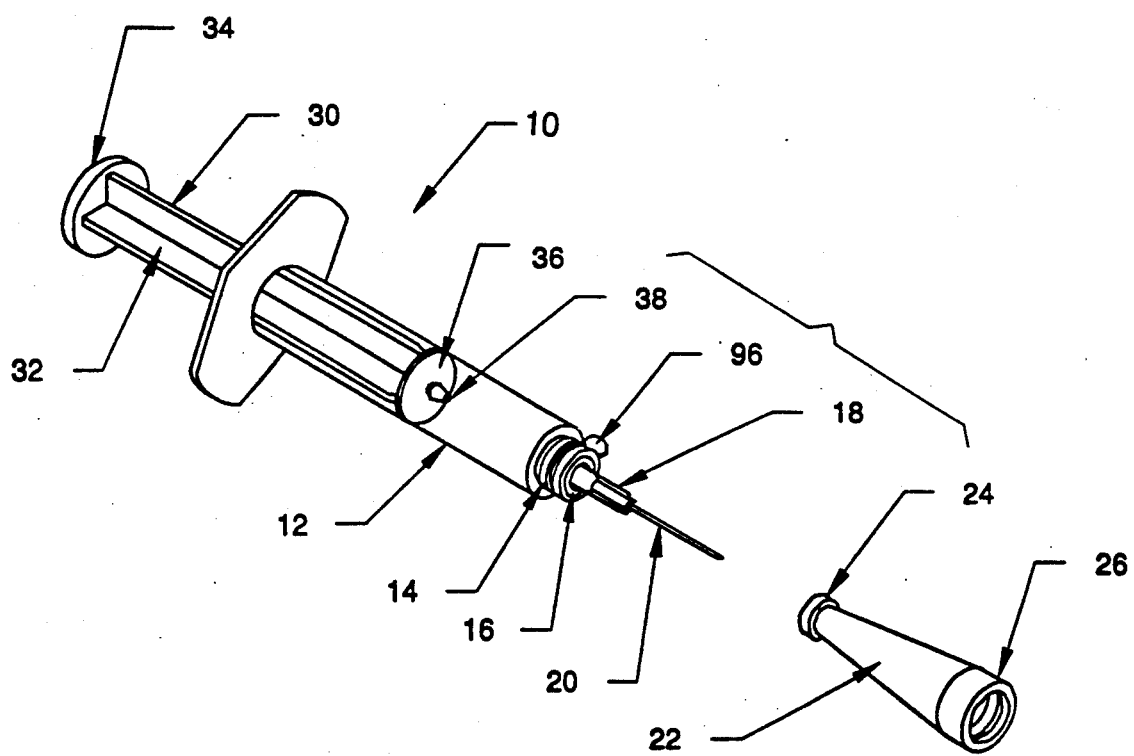
FIG. 1 is an isometric view of one alternative embodiment of a retractable syringe according to the present invention, the syringe being shown in assembled condition and ready for use.

Referring initially to FIGS. 1 and 2, one alternate embodiment of the retractable syringe of the present invention is shown generally at 10. Syringe 10 includes a resilient barrel 12, the proximal end, that is, the end nearer the point of the needle, of which comprises a needle carrier support or mounting collar 14. A needle carrier 16, more particularly described below and better shown in FIGS. 3-5 and 8, is mounted within needle carrier support or mounting collar 14. Needle carrier 16 is adapted to support therewithin a needle cartridge 18 in which is mounted a hypodermic needle 20. An invertible locking safety cover 22 is adapted at one end 24 to be frictionally retained on needle cartridge 18, covering needle 20, prior to use of syringe 10, and at the other end 26 to be positively locked to the hub 28 of mounting collar 14 prior to installation of a needle cartridge 18 into needle carrier 16, and after use of syringe 10 and retraction of needle 20 into barrel 12, as more particularly described below.

An elongate plunger member 30 is telescoped into and carried within the barrel 12. Plunger member 30 includes a body portion comprising a plurality of longitudinally extending ribs 32, a thumb rest 34 formed at its distal end, that is, the end farther from the point of the needle, and an injection piston 36 attached at its proximal end, disposed within barrel 12. The proximal face of piston 36 includes a longitudinally extending stinger latch 38 at or near its center.

Plunger 30 including piston 36 may be made of a relatively hard material such as, for example, high density polypropylene or other suitable synthetic material. The outer circumferential periphery of piston 36 is substantially smooth and rounded to provide sealing engagement against the interior wall of barrel 12. Barrel 12 may be made of a relatively resilient material such as polyethylene or polypropylene, for example. The same material used for barrel 12 may also be employed for protective cover or sheath 22. All materials should be of a grade and quality suitable for human medical applications.

Piston 36 is of slightly larger diameter than the inside diameter of barrel 12 so that in service, the barrel is slightly stretched by the piston 36 as the piston traverses the barrel in sealing relationship therewith. Piston 36 is sized and shaped to serve as a liquid or fluid displacement means within barrel 12 for withdrawing a liquid or fluid substance from another container, for example, and subsequently injecting the substance through needle 20 into a subject being treated. Of course, syringe 10 may be used for withdrawing liquid or fluid substances from a subject for subsequent testing, or for other purposes. In short, the retractable syringe 10 of the present invention may be used in any clinical setting, under any medical conditions.

Figure 5:
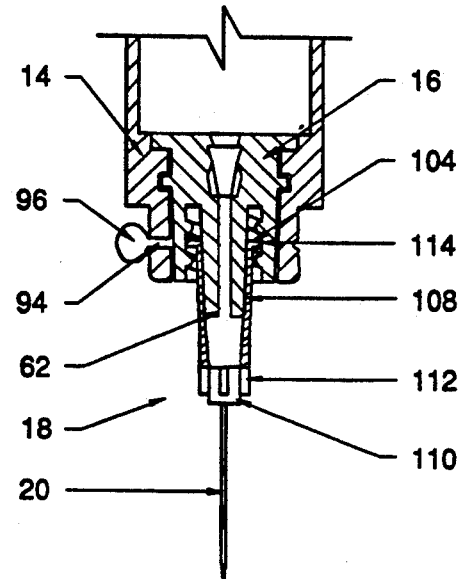
FIG. 5 is a vertical sectional view of the assembled mounting collar, needle carrier, and needle cartridge of the embodiment of FIG. 1.

Referring now to FIGS. 3-5, needle carrier 16 is mounted within mounting collar 14 of barrel 12 from within the barrel, and needle cartridge 18 is subsequently mounted to the proximal end of needle carrier 16 from outside barrel 12. Needle carrier 16 has a generally circular conical main body 40 with a slight taper from its distal end 42 to its proximal end 44. A radially outwardly extending circumferential flange 46 is disposed around body 40 at its distal end 42. A plurality of radially outwardly extending bayonet lugs 48 are disposed on the exterior side wall of body 40 between flange 46 and proximal end 44. Preferably, there are two such lugs 48 which are diametrically opposed from one another. A latch recess 50 extends into body 40 of needle carrier 16 from its distal end 42. Latch recess 50 is shaped correlatively to stinger latch 38, as is more fully set out below.

Figure 7:
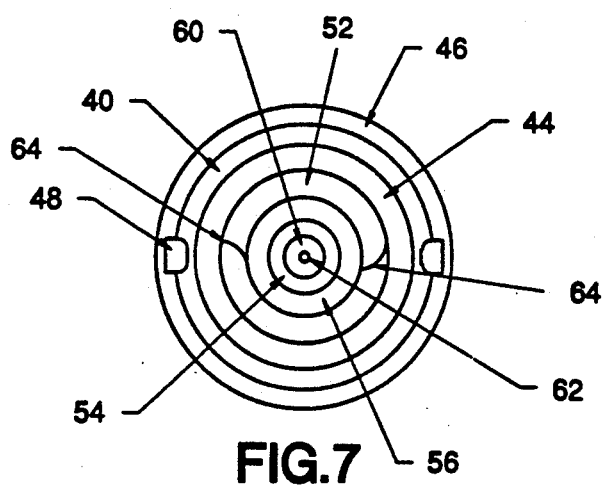
FIG. 7 is an end view of the needle carrier of both the first and second alternative embodiments of the invention described herein, taken along lines 7—7 of FIGS. 3 and 11.

A substantially annular blind bore 52, comprising a needle cartridge receiving pocket, extends longitudinally part way, preferably about half way, through main body 40 from its proximal end 44. In the center of pocket 52 there is disposed a needle cartridge support member 54, which may be integral, for example, with main body 40. Needle cartridge support member 54 extends from the distal end wall 56 of pocket 52 beyond the plane of the proximal end face 44 of main body 40, such that a substantial proximal end portion of member 54 protrudes out of the main body 40. Needle cartridge support member 54 is substantially circular conical in configuration, and tapers slightly from its distal end at end wall 56 to its proximal end 60. Needle cartridge support member 54 has a longitudinally extending central axial bore 62 therein, in fluid communication with latch recess 50. Pocket 52 has a pair of relatively steeply pitched, raised, that is, radially inwardly projecting, axially spaced apart helical ribs 64 around its outer wall, forming a pair of lands upon which a corresponding pair of tabs disposed on the distal end of the needle cartridge 18 ride in removing or installing the needle cartridge, as is more fully set out below. The ribs 64 begin, or intersect the proximal end face of main body 40, on diametrically opposed sides thereof as is best shown in FIG. 7.

Mounting collar 14 includes a hub portion 28 extending from the proximal end 70 thereof to a relatively thick-walled needle carrier retaining portion 72 of barrel 12, forming an annular shoulder 74 therebetween. The hub portion 28 and needle carrier retaining portion 72 of barrel 12 have a substantially circular conical bore 76 therethrough, shaped correlatively to the outer profile of main body 40 of needle carrier 16. Between the upper or distal end of bore 76 in needle carrier retaining portion 72 and the interior wall 78 of barrel 12 against which piston 36 is sealingly engaged, is disposed a circular counterbore 80. Flange 46 of needle carrier 16 is received in counterbore 80 when the needle carrier 16 is locked in place in mounting collar 14. Flange 46 is somewhat resilient, so that it will sealingly engage counterbore 80 when carrier 16 is locked into place in collar 14.

Mounting collar 14 has a pair of diametrically opposed, substantially longitudinally extending slots 82 in the wall of bore 76, extending in a proximal direction from the interface between bore 76 and counterbore 80. Slots 82 intersect and communicate with a pair of inclined recesses or threads 84 in the wall of bore 76 which extend part way, for example 90° or less, around the inside wall of bore 76 and are inclined toward the proximal end 70 of hub portion 28. Threads 84 as shown are right-hand threads, but left-hand threads could be used, as desired. Threads 84 each have a friction rise or bump 86 on their proximal surfaces near their blind ends. Slots 82 are adapted to receive bayonet lugs 48 on needle carrier 16, and when the needle carrier is so inserted into collar 14 and rotated in the proper direction, preferably 90° or less, lugs 48 traverse the buttresses of threads 84 until they bottom out at the blind ends of the threads. Due to the inclined nature of threads 84, rotation of the needle carrier to the right (for a right-hand thread 84) will tend to draw the needle carrier 16 more tightly into the mounting collar 14, and will tend to energize the seal between flange 46 and counterbore 80.

Somewhat more force is required to pass lugs 48 over friction rises or bumps 86 in either direction than is required simply to rotate needle carrier 16 in collar 14 with the lugs traversing the threads 84 between slots 82 and the friction rises or bumps. Accordingly, when the lugs 48 are fully seated in the blind ends of threads 84, bounded on one side by the blind end walls of the threads 84 and on the other side by the friction rises or bumps 86, the lugs 48 will be relatively securely seated in the blind ends of threads 84, and the needle carrier 16 will in turn be relatively securely latched into the mounting collar 14. Bumps 86 thus act as anti-rotation means between mounting collar 14 and needle carrier 16. Bumps 86 may not be necessary, however, if sufficient frictional forces exist between needle carrier 16 and mounting collar 14 to prevent relative rotation between them during installation and/or removal of a needle cartridge as discussed further below.

FIG. 4 illustrates the needle carrier 16 fully seated and latched into collar 14. Such installation and latching occurs within barrel 12 as the syringe 10 is being assembled prior to use. FIG. 4 shows the needle carrier 16 in the same position depicted in FIG. 3, but the mounting collar 14 has been rotated, preferably, as stated above, 90° or less. As can be seen in FIG. 4, needle carrier 16 has a transversely disposed hole 90 extending through the side wall of main body 40 into pocket 52. Mounting collar 14 has a transversely disposed hole 92 extending through the side wall of hub portion 28. Holes 90, 92 are in register with one another when the needle carrier 16 is fully latched into the mounting collar 14. Hole 92 in collar 14 is substantially circular cylindrical in configuration, but hole 90 in needle carrier 16 is preferably somewhat elongated in a circumferential direction in order to ensure alignment of holes 90, 92 in the event needle carrier 16 is not fully seated in collar 14. A retaining pin 94 is disposed in holes 90, 92, and frictionally secured in hole 92, when needle carrier 16 is fully mounted in collar 14 in order to prevent relative rotation between members 14, 16 in service, e.g., prior to and during use of syringe 10 to withdraw and/or inject fluids or liquid substances, and prior to desired retraction of needle 20 into barrel 12 Pin 94, when in place in holes 90, 92, thus serves to prevent needle carrier 16 from being accidentally or prematurely released or unlatched from collar 14 and retracted into barrel 12. A tab 96 is provided on the end of pin 94 for an operator to grasp for easy removal of pin 94 when it is desired to retract the needle carrier 16, and hence the needle 20, into barrel 12 after use of syringe 10. It should be understood that retaining pin 94, and thus bores 90, 92, may not be necessary in the event that sufficient frictional forces exist between needle carrier 16 and mounting collar 14 to prevent relative rotation of such members during installation and/or removal of a needle cartridge.

Mounting collar 14 further includes a circumferentially extending groove 98 around the periphery of hub portion 28 and adapted to receive a correlatively shaped ridge or land 100 disposed on locking safety cover 22, as more fully described hereinafter.

Referring now particularly to FIGS. 2, 5, 6, and 8, the needle cartridge 18 of the present invention is shown in more detail. Needle cartridge 18 includes an elongate, generally conical, hollow main body 102 which tapers slightly from its upper or distal end 104 to its lower or proximal end 106. Main body 102 of needle cartridge 18 has a tapered, longitudinally extending, central axial bore 108 which has a taper substantially the same as the taper of the outside surface of needle cartridge support member 54, so as to form a close fit therewith when installed on syringe 10. Bore 108 is in fluid communication with bore 62 in needle cartridge support member 54. Needle cartridge 18 also includes a substantially circular cylindrical extension portion 110 extending in a proximal direction from proximal end 106 of main body 102. A plurality of substantially longitudinally extending stiffening ribs 112 are disposed on main body 102 and extension portion 110 along their outer sides, there being preferably four (4) such ribs 112 disposed at substantially 90° to one another. Cylindrical extension 110 of needle cartridge 18 has a central axial bore therethrough, which is in fluid communication with bore 108 of main body 102. A hypodermic needle 20 of selected size and shape is mounted within the central axial bore in cylindrical extension 110. Needle 20 has a longitudinally extending bore therethrough of selected diameter, which bore is in fluid communication with bore 108 and, hence, bore 62 in needle cartridge support member 54.

Figure 6:
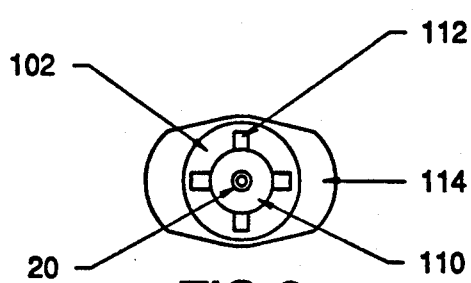
FIG. 6 is an end view of the needle cartridge of both the first and second alternative embodiments of the invention described herein, taken along lines 6—6 of FIGS. 2 and 10.

The upper or distal end 104 of needle cartridge 18 includes a pair of diametrically opposed, outwardly extending tabs or ears 114 (FIG. 6). When the distal end 104 of needle cartridge 18 is inserted longitudinally axially into needle carrier 16 from the proximal end thereof and rotated to the right (for a right hand thread 64; to the left for a left-hand thread), each of tabs 114 engages and travels along one of the helical threads 64, which draws needle cartridge 18 onto needle cartridge support member 54 and forces the needle cartridge into secure, stable, sealed relationship with the needle cartridge support member. The tight frictional engagement of tabs 114 against the walls of pocket 52 provides additional lateral stability and support of needle cartridge 18 when mounted in needle carrier 16. When needle cartridge 18 is rotated or screwed into locked position in needle carrier 16, anti-rotation pin 94 prevents needle carrier 16 from rotating in mounting collar 14 and becoming unlatched therefrom. In order to remove needle cartridge 18 from needle carrier 16, for example, to replace it with a different shaped or sized needle, as desired, the needle cartridge is rotated to the left (for a right-hand thread 64; to the right for a left-hand thread), and tabs 114 travel along threads 64 until they are released therefrom at or near proximal end 44 of main body 40. Again, anti-rotation pin 94 prevents relative rotation between members 14, 16 when removing needle cartridge 18 from needle carrier 16. It should be understood, however, that depending upon whether threads 64, 84 are right-hand, left-hand or one of each, either the removal of needle cartridge 18 from needle carrier 16 or the installation of needle cartridge 18 onto needle carrier 16, will tend to rotate the members 14, 16 with respect to one another in a direction so as to further engage lugs 48 into threads 84.

Figure 8:
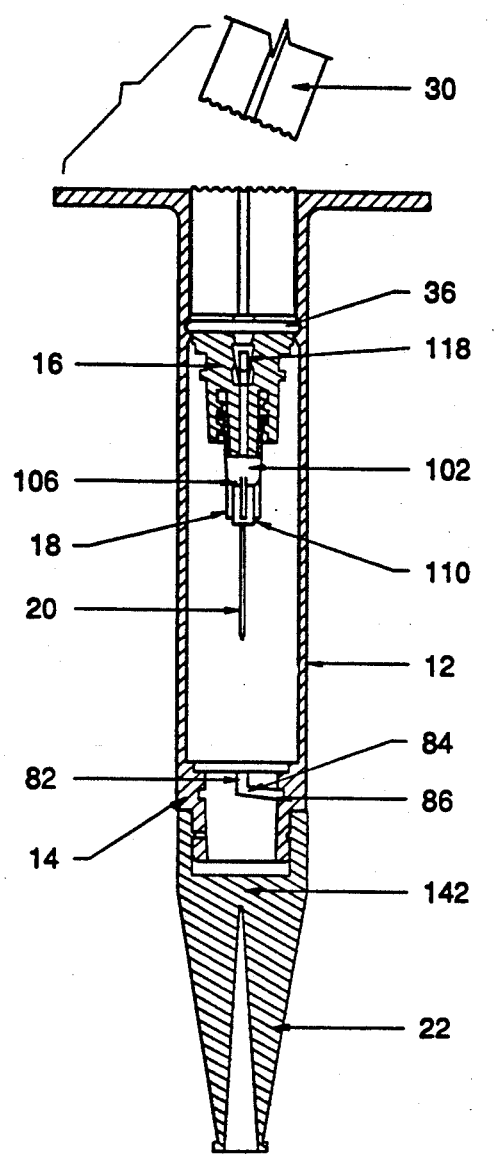
FIG. 8 is a vertical sectional view of the embodiment shown in FIG. 1, after use of the syringe and retraction of the needle cartridge and needle into the syringe barrel.

Referring now particularly to FIGS. 2, 5, and 8, stinger latch 38 of piston 36 has a main body 39 of generally conical configuration with a retaining lip 116 around its upper periphery. Stinger latch 38 also includes a pair of rotational lugs 118 extending longitudinally axially from below lip 116 to the proximal end or apex of main body 39. Rotational lugs 118 are disposed on diametrically opposed sides of stinger latch 38. Stinger latch 38 is adapted to stretch an inner shoulder 120 of the resilient flange 46 and to descend into recess 50 formed in the distal end of needle carrier 16 when plunger 30 is advanced to the proximal end of its stroke. Stinger latch 38 is thus stabbed into engagement with a tapered latch seat 122 in recess 50. Recess 50 has correlatively shaped grooves 124 extending longitudinally axially on opposite sides of latch seat 122 for receiving rotational lugs 118. When stinger latch 38 is pushed into the recess 50 of needle carrier 16 in substantially random angular orientation with respect thereto, latch 38 may be rotated slightly one way or the other in order to bring lugs 118 into engagement with grooves 124 of recess 50. When lugs 118 have so engaged grooves 124, further rotation of plunger member 30 will rotate piston 36, stinger latch 38, needle carrier 16, needle cartridge 18, and needle 20. Rotation of needle carrier 16 in mounting collar 14 will be prevented, however, if retaining pin 94 remains in aligned bores 90, 92. Rotation of needle carrier 16 in mounting collar 14 will be further retarded by friction bumps 86 following removal of pin 94.

When retaining pin 94 is removed from bores 90, 92, further rotation of the plunger member 30 and injection piston 36 in the appropriate direction also rotates the needle carrier 16 and its lugs 48 along the threads 84 until the lugs are in alignment with slots 82, whereupon withdrawal of the piston 36 back into the barrel 12 also withdraws the needle carrier 16, needle cartridge 18, and needle 20 as a unit back into the barrel 12, eliminating the possibility of a needle stick injury.

The upper or distal end of barrel 12 has an annular area or land 130 of reduced inside diameter. An annular latching groove 132 is formed in land 130 near its proximal end, adjacent to an annular latching rib 134 disposed proximally of latching groove 132. The latching groove 132 is of about the same inside diameter as the barrel 12 below land 130. Like land 130, the annular latching rib 134 has an inside diameter smaller than the inside diameter of barrel 12 below land 130; the inside diameter of rib 134 may, for example, be about the same as land 130. When piston 36 is withdrawn into barrel 12 in order to retract needle 20 into the barrel, and as the piston is pulled against the rib 134, the rib will stretch and permit the rounded edge of the piston to pass over it into seated position in latching groove 132. Since the thickness of rib 134 is greater than that of the wall of barrel 12 below the rib, considerably greater force is required to stretch the rib outwardly than is required to stretch the barrel wall. Accordingly, somewhat greater force is required to pull the piston 36 over the rib 134 than is required to withdraw the piston through the barrel. Once seated in latching groove 132, piston 36 is substantially resistant to movement in either direction. Although it is preferred to provide rib 134 and groove 132 to hold piston 36 in retracted position within barrel 12, the rib and groove may be omitted, and the frictional force due to the stretch of land 130 around piston 36 relied upon instead to hold the piston in place. Further, all of the rib, groove, and land may be omitted, because with the breaking off of the plunger, infra, the friction of the barrel against the piston may be sufficient to latch the needle in retracted position in the barrel.

Plunger member 30 is provided with perforations 136 in ribs 32 at a location such as to be substantially flush with the distal end of barrel 12 when piston 36 is seated in groove 132. Lateral force may then be applied to the distal end of plunger 30 to break off the plunger at the perforations 136, leaving the remainder of the plunger disposed inside barrel 12 with its distal end substantially flush with the distal end of the barrel 12. FIG. 8 illustrates the plunger being broken off in this manner.

The syringe 10 is delivered to the person who will use it either in the assembled configuration shown in FIG. 1, or in a similar configuration but without a needle cartridge and needle mounted thereon. If the syringe 10 is delivered in the assembled configuration shown in FIG. 1, the operator may proceed to use it as is, or he or she may choose to remove the needle cartridge and needle supplied with the particular syringe and replace it with another needle cartridge and needle. Such a situation might arise, for example, if the operator wishes to use a needle of a different shape, such as longer or shorter, or of a different size, such as with a larger or smaller diameter and/or bore. If the operator wishes to replace the needle cartridge and needle, he or she grasps the needle cartridge firmly around the main body 102 and ribs 112 and rotates it in the appropriate direction to unscrew the cartridge 18 from the needle carrier pocket 52. Preferably, during this removal and replacement procedure a locking safety cover 22 remains on the needle cartridge being removed and on the needle cartridge being installed in its place. Locking safety covers 22 at this stage of the procedure will have their smaller ends 24 frictionally retained around the proximal ends of main bodies 102 and ribs 112 of needle cartridges 18, with needles 20 being safely received in tapered blind bores 138 of covers 22 (FIG. 2). After removing the supplied needle cartridge, the operator then installs the desired needle cartridge by grasping it firmly, preferably with its cover 22 in place, inserting its distal end into pocket 52 with member 54 entering bore 108, and rotating it in the appropriate direction to screw it securely into place as shown, for example, in FIGS. 5 and 8, so that it is integral.

If the syringe 10 were to be supplied with no needle cartridge 18 installed thereon, the operator simply has to install a desired needle cartridge as set out above so that it is integral. In order to ensure that a syringe 10 supplied without a needle cartridge is not contaminated prior to the time a needle cartridge is installed, it is preferred that a locking safety cover 22 be installed on the hub 28 of mounting collar 14, as shown, for example, in FIG. 8, when the syringe 10 is manufactured so as to protectively enclose the barrel. For this purpose the larger end 26 of cover 22 is provided with an axially extending blind bore 140 of a shape correlative to that of hub 28 and a diameter slightly smaller than the outside diameter of the hub, so that when the cover is forced over the hub, the cover will stretch slightly and sealingly engage the hub. Annular locking ridge or land 100 of cover 22 will engage and seat in annular groove 98 around hub 28 in order to positively retain cover 22 on hub 28. A fluid barrier 142 between blind bore 140 and tapering bore 138 of cover 22 prevents fluid communication between the bores.

During the time that a needle cartridge is either removed or installed, i.e., prior to use of the syringe, the retaining pin 94 remains in place in bores 90, 92 in order to prevent needle carrier 16 from rotating in mounting collar 14. When the desired needle cartridge is fully installed and in place in needle carrier 16, syringe 10 is ready for use. Piston 36 is free to be moved by plunger 30 from below rib 134 to a position just short of latching engagement between stinger latch 38 and needle carrier 16. The operator may then remove cover 22 from needle cartridge 18 and needle 20, and proceed to either draw a liquid or fluid substance from a container through needle 20 into barrel 12 and inject it into a subject, or insert the needle 20 into a subject with barrel 12 empty and withdraw blood or other fluids from the subject for depositing into a container for testing or the like.

After the syringe 10 has been used, plunger member 30 is pushed firmly in a proximal direction until latch 38 of piston 36 is forced into recess 50 in needle carrier 16, and the plunger is rotated slightly one way or the other, if necessary, so that lugs 118 of latch 38 seat in grooves 124 of recess 50. Engagement of latch 38 in recess 50 is shown, for example, in FIG. 2. Pin 94 is then removed from needle carrier 16 and hub 28, and the plunger 30 is rotated in the appropriate direction to move lugs 48 along threads 84 into register with slots 82. Since lugs 48 will initially be relatively securely seated between friction rises 86 and the ends of threads 84 prior to rotation of needle carrier 16, somewhat greater force will be necessary to rotate the lugs over the friction rises than will be required to continue rotating the lugs over the remainder of the threads 84 to slots 82.

The plunger head 34 is then pulled in a distal direction to pull needle carrier 16, needle cartridge 18, and needle 20 into barrel 12 until piston 36 travels over rib 134 and seats in groove 132. Whether or not groove 132 is used, the distal portion of the plunger member 30 is broken off at perforations 136 and discarded, leaving the broken end of the plunger substantially flush with the end of the barrel and if groove 132 is used, the remainder of the plunger securely latched within the barrel 12. The needle cartridge 18 and needle 20 are thus securely retained and immobilized in protective isolation within the barrel, as shown in FIG. 8. The protective cover 22 may then be installed on the hub 28 of collar 14 as shown in FIG. 8 in order to prevent excess fluids or residue remaining in the syringe 10 from leaking out of the syringe. The used syringe may then be safely discarded without further danger of a needle stick injury.

Figure 9:
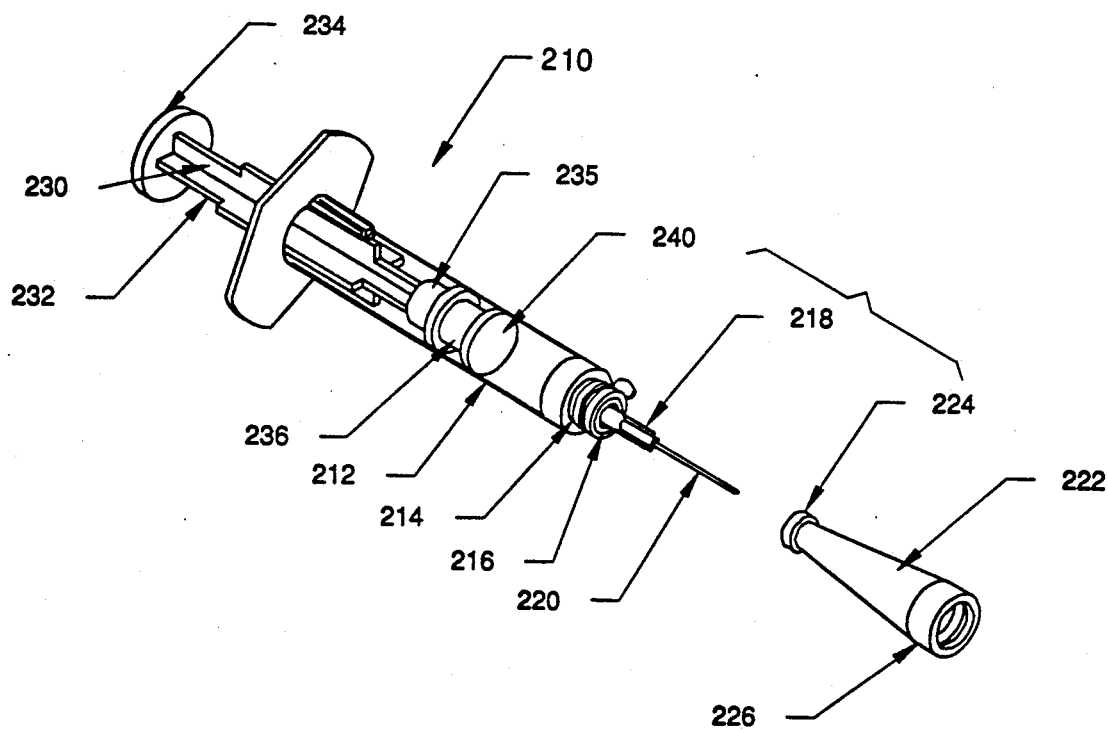
FIG. 9 is an isometric view of a second alternative embodiment of a retractable syringe according to the present invention, the syringe being shown in assembled condition and ready for use.
Figure 10:
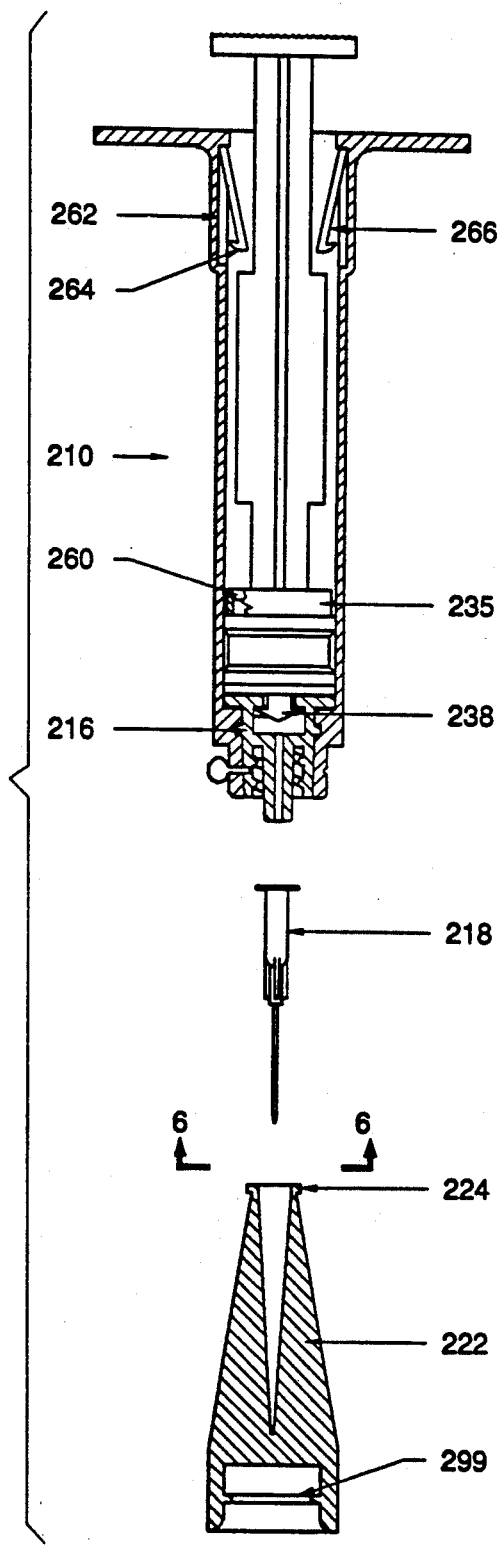
FIG. 10 is a view partly in longitudinal section, partly exploded, and partly in elevation of the retractable syringe of FIG. 9, showing the needle cartridge separated from the needle carrier and the protective cover removed from the needle cartridge, and showing the plunger latch disposed in the recess in the upper end of the needle carrier.
Figure 11:
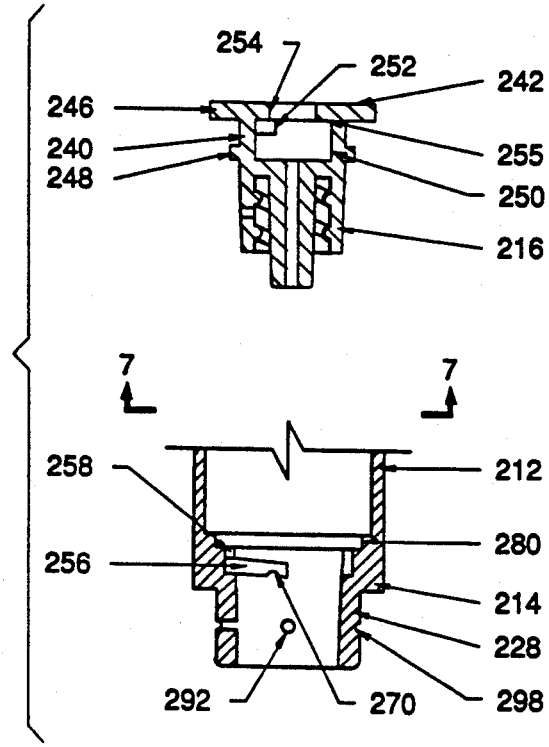
FIG. 11 is a vertical sectional view of the mounting collar and needle carrier of the embodiment of FIG. 9 in exploded relation with the needle carrier in position to be inserted into the mounting collar.
Figure 12:
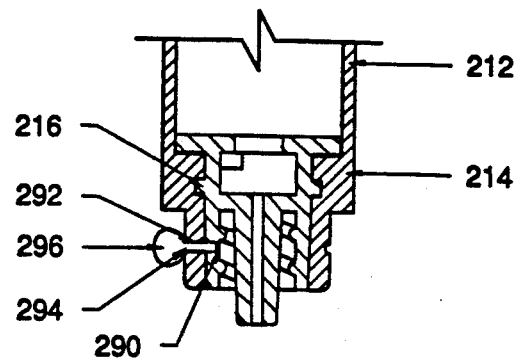
FIG. 12 is a vertical sectional view of the assembled mounting collar and needle carrier of the embodiment of FIG. 9.

Referring now to FIGS. 9 and 10, another alternate embodiment of the retractable syringe of the present invention is shown generally at 210. Syringe 210 includes a barrel 212, which may be non-resilient, the proximal end of which comprises a needle carrier support or mounting collar 214. A needle carrier 216, more particularly described below and better shown in FIGS. 11-13, is mounted within mounting collar 214. Needle carrier 216 is adapted to support therewithin a needle cartridge 218 in which is mounted a hypodermic needle 220. An invertible locking safety cover 222 is adapted at one end 224 to be frictionally retained on needle cartridge 218, covering needle 220, prior to use of syringe 210, and at the other end 226 to be positively locked to the hub 228 of mounting collar 214 prior to installation of a needle cartridge 218 into needle carrier 216, and after use of syringe 210 and retraction of needle 220 into barrel 212, as more particularly described below.

The needle cartridge 218, needle 220, protective cover 222, and mounting collar 214 of syringe 210 are substantially identical to the corresponding parts of the syringe 10, i.e. needle cartridge 18, needle 20, protective cover 22, and mounting collar 14, and thus will not be described again in detail in connection with the second embodiment.

An elongate plunger member 230 is telescoped into and carried within the barrel 212. Plunger member 230 includes a body portion comprising a plurality of longitudinally extending ribs 232, a thumb rest 234 formed at its distal end, and an inwardly facing latching flange 235 and plunger head (not shown) attached at its proximal end, disposed within barrel 212. The plunger head may be of any suitable shape, such as, for example, a pair of conical frustums attached end to end at their smaller circular faces and coaxially disposed with respect to the plunger body, and is disposed within and retains thereon an injection piston 236. A plunger latch 238 (FIGS. 10 and 14) is attached to the plunger head at or near the center of its proximal end. Piston 236 is preferably made of a soft resilient material such as soft rubber, butyl, latex, or the like, and is of a shape and size to serve as a liquid or fluid substance displacement piston sealed by its elastomer type deformation within barrel 212 for the same purposes as piston 36 described above.

Referring now to FIGS. 11-13, needle carrier 216 is mounted within mounting collar 214 of barrel 212 from within the barrel, and needle cartridge 218 is subsequently mounted to the proximal end of needle carrier 216 from outside barrel 212. Except for the manner and structure in and by which the needle carrier 216 is engaged by the plunger latch 238 to release the needle carrier from the mounting collar 214, needle carrier 216 is substantially the same as needle carrier 16. For the sake of clarity and brevity, the manner and structure in and by which the needle carrier 216 is mounted in and released from collar 214, and the needle cartridge 218 is mounted in and released from needle carrier 216, will not be described again in detail in connection with the second embodiment; suffice it to say that these matters are substantially identical to the manner and structure in and by which the needle carrier 16 is mounted in and released from collar 14, and the needle cartridge 18 is mounted in and released from needle carrier 16.

A latch recess 250 extends into the body 240 of needle carrier 216 from its distal end 242. Latch recess 250 is a generally rectangular cavity into which projects a pair of oppositely facing plunger latch stops 252 formed in body 240 near the distal extremity of cavity 250 and spaced apart so as to form rotational stops at 180° from one another. An opening 254 in the distal end of needle carrier 216, smaller than cavity 250, communicates cavity 250 with the distal end surface of body 240 and forms a shoulder 255 therebetween. A circular counterbore 280 of mounting collar 214 sealingly receives an annular resilient flange 246 of needle carrier 216 when the needle carrier 216 is locked in place in mounting collar 214.

FIG. 12 illustrates the needle carrier 216 fully seated and latched into collar 214. Such installation and latching occurs within barrel 212 as the syringe 210 is being assembled prior to use. FIG. 12 shows the needle carrier 216 in the same position depicted in FIG. 11, but the mounting collar 214 has been rotated, preferably 90° or less. As can be seen in FIG. 12, a retaining pin 294 is disposed in aligned holes 290, 292 in needle carrier 216 and collar 214, respectively, and is frictionally secured in hole 292, when needle carrier 216 is fully mounted in collar 214 in order to prevent relative rotation between members 214, 216 in service, e.g., prior to and during use of syringe 210 to withdraw and/or inject fluids or liquid substances, and prior to desired retraction of needle 220 into barrel 212. Pin 294 is substantially identical to pin 94, and when in place in holes 290, 292, thus serves to prevent needle carrier 216 from being accidentally or prematurely released or unlatched from collar 214 and retracted into barrel 212. A tab 296 is provided on the end of pin 294 for an operator to grasp for easy removal of pin 294 when it is desired to retract the needle carrier 216, and hence the needle 220, into barrel 212 after use of syringe 210. As in the case of the first embodiment described above, pin 294 may not be necessary if sufficient antirotational forces exist between needle carrier 216 and mounting collar 214 when assembled.

Mounting collar 214 further includes a circumferentially extending groove 298 around the periphery of hub portion 228 of collar 214 and adapted to receive a correlatively shaped ridge or land 299 disposed on locking safety cover 222, as more fully described hereinafter.

The proximal end of piston 236 may be formed as a thin diaphragm 240 (FIG. 9) which covers the plunger latch 238 in sealed relation during the time the piston is used to draw liquids or fluid substances into barrel 212 or to force such liquids or fluid substances out of barrel 212, as discussed above with respect to the first embodiment of the present invention. Alternatively, the piston 236 may be made with the neck of the plunger latch 238 protruding from the proximal end of the piston at all times. If the diaphragm 240 is present, the plunger latch 238 is pushed to stretch and distend the diaphragm into recess 250 formed in needle carrier 216, and the plunger member 230 is rotated to rotate the plunger latch 238 into engagement with plunger latch stops 252. Diaphragm 240 may be ruptured at times. If diaphragm 240 is not present, plunger latch 238 is simply pushed into recess 250 and rotated into engagement with plunger latch stops 252. Further rotation of the plunger head and latch 238 also rotates the needle carrier 216 and its lugs 248 along the threads 256 until the lugs are in alignment with slots 258, whereupon withdrawal of the plunger head back into the barrel 212 also withdraws the needle carrier 216 and needle cartridge 218 along with needle 220 as a unit back into the barrel, eliminating the possibility of a needle stick injury. As the plunger 230 is pulled away from the distal end of the barrel 212, the plunger head and the piston 236 are also pulled along as a connected unit.

Latch flange 235 comprises a body of generally hollow circular cylindrical side wall configuration with a radially inwardly extending, downwardly and inwardly tapering, annular frustoconical latch flange 260 disposed around its upper inner periphery. The upper end of barrel 212 is provided with recessed pockets 262 which accommodate at least two latch hooks 264 carried on latch arms 266 (FIG. 10). Piston 236 is inserted into the barrel 212 as the syringe 210 is assembled. Latch arms 266 carry the latch hooks 264 out into a position where the latch flange 260 will flex the arms 266 inwardly in moving in a distal direction past hooks 264, then will engage the hooks 264 to prevent movement of the piston 236 in a proximal direction back toward support collar 214. Thus, when piston 236 is retracted, and when the plunger head has carried the needle carrier 216, needle cartridge 218, and needle 220 back into the protected position within barrel 212, the hooks 264 are latched onto the flange 260. Thereafter, the needle carrier 216 and plunger head are prevented from return movement. The plunger may also be broken off, with or without use of the hooks 264 system, for use as in the first embodiment to fix the needle location.

The syringe 210 is delivered to the person who will use it either in the assembled configuration shown in FIG. 9, or in a similar configuration but without a needle cartridge and needle mounted thereon. If the syringe 210 is delivered in the assembled configuration shown in FIG. 9, the operator may proceed to use it as is, or he or she may choose to remove the needle cartridge and needle supplied with the particular syringe and replace it with another needle cartridge and needle, for reasons set out above in connection with the description of the first embodiment, for example. If the operator wishes to replace the needle cartridge and needle, he or she follows the same procedure set out above in connection with the first embodiment. It should be noted again that preferably, during this removal and replacement procedure a locking safety cover 222 remains on the needle cartridge being removed and on the needle cartridge being installed in its place.

If the syringe 210 were to be supplied with no needle cartridge 218 installed thereon, the operator simply has to install a desired needle cartridge as set out above. In order to ensure that a syringe 210 supplied without a needle cartridge is not contaminated prior to the time a needle cartridge is installed, it is preferred that a locking safety cover 222 be installed on the hub 228 of mounting collar 214, as shown, for example, in FIG. 14, when the syringe 210 is manufactured so as to protectively enclose the barrel. Annular locking ridge or land 299 of cover 222 will engage and seat in annular groove 298 around hub 228 in order to positively retain cover 222 on hub 228.

During the time that a needle cartridge is either removed or installed, i.e., prior to use of the syringe, the retaining pin 294, if employed, remains in place in bores 290, 292 in order to prevent needle carrier 216 from rotating in mounting collar 214. As stated above, friction bumps 270, like bumps 86, also serve as anti-rotation means between collar 214 and needle carrier 216. When the desired needle cartridge is fully installed and in place in needle carrier 216, syringe 210 is ready for use. Piston 236 is free to be moved by plunger 230 from below pockets 262 to a position before the diaphragm 240, if present, is stretched or punctured (although this is not desirable without further sealing), or otherwise before latch 238 is engaged into recess 250. The operator may then remove cover 222 from needle cartridge 218 and needle 220, and proceed to either draw a liquid or fluid substance from a container through needle 220 into barrel 212 and inject it into a subject, or insert the needle 220 into a subject with barrel 212 empty and withdraw blood or other fluids from the subject for depositing into a container for testing or the like.

After the syringe 210 has been used, plunger member 230 is pushed firmly in a proximal direction into engagement with needle carrier 216 sufficiently to stretch or rupture the diaphragm 240, if present, and force the latch 238 of piston 236 into recess 250 in needle carrier 216 (FIG. 10). Plunger 230 is then rotated in the appropriate direction until latch 238 engages latch stops 252, whereupon further rotation of the plunger head and latch against stops 252 will also rotate needle carrier 216 when retainer pin 294 is removed from bores 290, 292. Engagement of latch 238 in recess 250 is shown, for example, in FIG. 10. Pin 294 is then removed from needle carrier 216 and hub 228, and the plunger 230 is rotated further in the appropriate direction t move lugs 248 along threads 256 into register with slots 258. Since lugs 248 will initially be relatively securely seated between friction rises 270 and the ends of threads 256 prior to rotation of needle carrier 216, somewhat greater force will be necessary to rotate the lugs 248 over the friction rises than will be required to continue rotating the lugs 248 over the remainder of the threads 256 to slots 258.

The plunger head 234 is then pulled in a distal direction to pull needle carrier 216, needle cartridge 218, and needle 220 into barrel 212 until latch flange 260 has become latched to hooks 264 (FIG. 14). Plunger member 230 may also be provided with perforations in ribs 232 so that the distal portion of the plunger member may be broken off at the perforations and discarded, leaving the broken end of the plunger substantially flush with the end of the barrel and the remainder of the plunger securely latched within the barrel 212. The needle cartridge 218 and needle 220 are thus securely retained and immobilized in protective isolation within the barrel, as shown in FIG. 14. The protective cover 222 may then be installed on the hub 228 of collar 214 as shown in FIG. 14 in order to prevent excess fluids or residue remaining in the syringe 210 from leaking out of the syringe. The used syringe may then be safely discarded without further danger of a needle stick injury.

Figure 15:
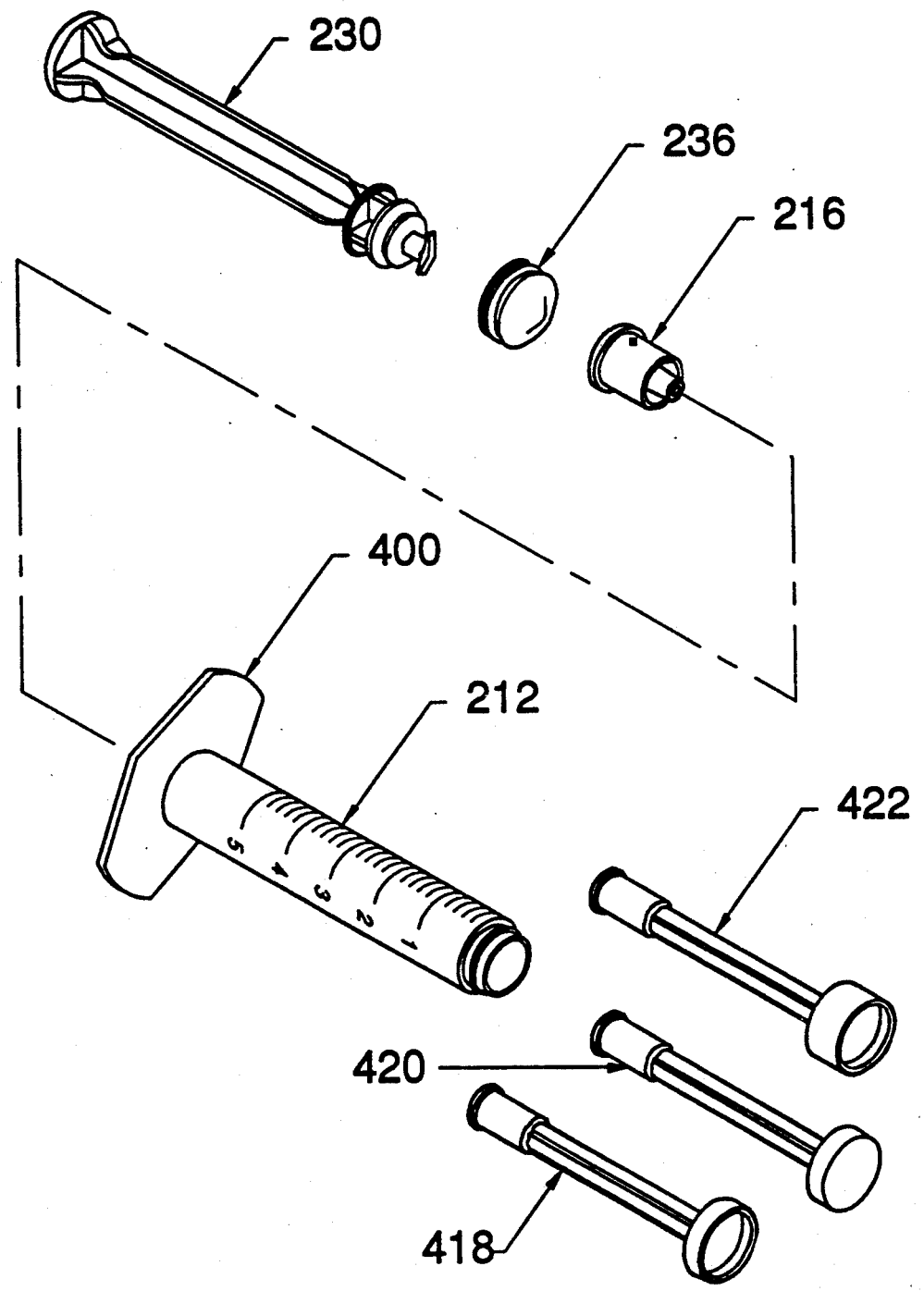
FIG. 15 is an isometric view of the preferred embodiment of a retractable syringe according to the present invention, the syringe being shown in exploded view with three types of alternate embodiment caps and without the syringe cartridge as in FIGS. 2 and 10.
Figure 17:
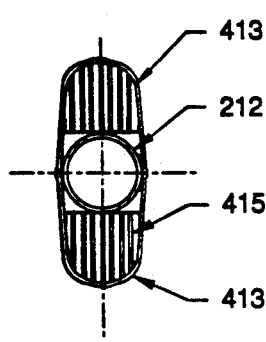
FIG. 17 is an end view of the barrel of FIG. 16 taken along section lines 17—17 of FIG. 2.
Figure 16:
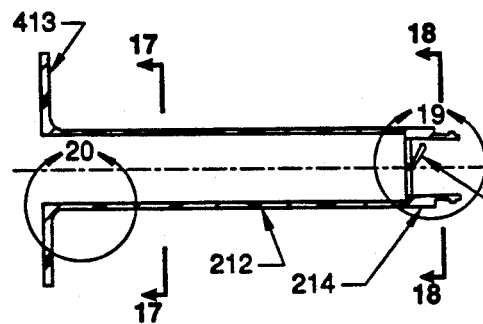
FIG. 16 is a longitudinal cross-sectional view of the preferred embodiment of the barrel of the retractable syringe of FIG. 15.
Figure 18:
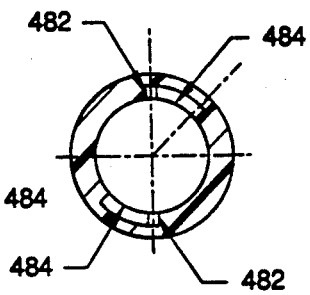
FIG. 18 is a cross-sectional view of FIG. 16 taken along section lines 18—18 of FIG. 16.
Figure 19:
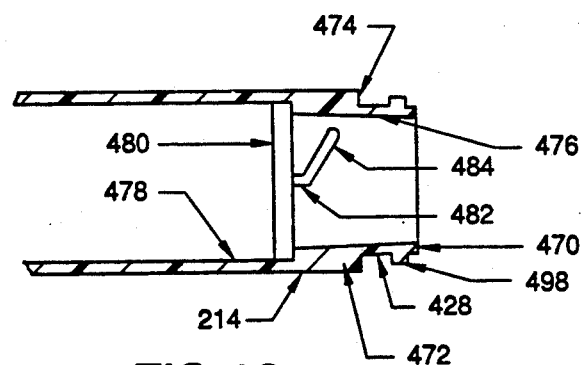
FIG. 19 is a detail view of the proximal end of the barrel of FIG. 16.
Figure 20:
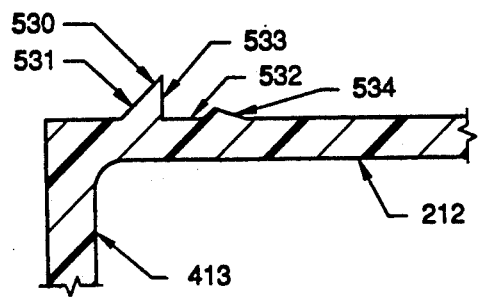
FIG. 20 is a detail view of the distal end of the barrel of FIG. 16.

Referring initially to FIG. 15, the preferred embodiment of the retractable syringe of the present invention is shown generally at 400. Syringe 400 includes a barrel 212, the proximal end of which comprises a needle carrier support or mounting collar 214. The distal end of barrel 212 includes a set of finger stops 413 having equally spaced grooves 415 formed therein to prevent finger skid.

A needle carrier 216, more particularly described below and better shown in FIGS. 29-34, when assembled as in the other embodiments is mounted within needle carrier support or mounting collar 214. Needle carrier 216 is adapted to support therewithin a needle cartridge 218 in which is mounted a hypodermic needle 220. An invertible locking safety cover 423, or alternatively 418, 420, or 422, is adapted at one end 224 (FIGS. 35, 38, 39) to have a mechanism in the preferred embodiment 423 to be frictionally retained on the hub 428 of mounting collar 214 prior to installation of needle cartridge 18 into needle carrier 216, or alternatively for covers 418, 210, 422 to be frictionally retained on needle cartridge 218, covering needle 20, prior to use of syringe 400, and at the other end 226 to be positively locked to the hub 428 of mounting collar 214 after use of syringe 400 and retraction of needle 220 into barrel 212, as more particularly described below (FIG. 43).

An elongate plunger member 230 is telescoped into and carried within the barrel 212 when assembled. Plunger member 230 includes a body portion comprising a plurality of longitudinally extending ribs 232 (FIG. 24) and a thumb rest 234 (FIG. 22) formed at its distal end. Thumb rest 234 includes grooves 427 to inhibit thumb slippage on thumb rest 234.

A retraction mechanism 421 (FIG. 25) is attached near the proximal end of plunger member 230, disposed within barrel 212 when assembled. The proximal face of retraction mechanism 421 includes a longitudinally extending retractor or stinger latch 238 at or near its center.

For retraction mechanism 421, stinger latch 238 is mounted on a mounting post 430 which extends from retractor pedestal 432. Retractor pedestal 432 is supported by mounting rim 434 seated on mounting base 436. Mounting base 436 terminates at flange 438. At the distal end of flange 438 there is located a sheer intent 440.

Figure 28:
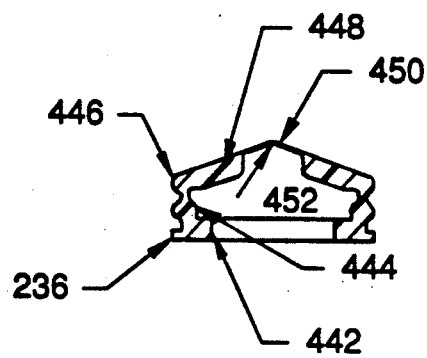
FIG. 28 is a cross-sectional view of FIG. 27 taken along section lines 28—28 of FIG. 27.
Figure 27:
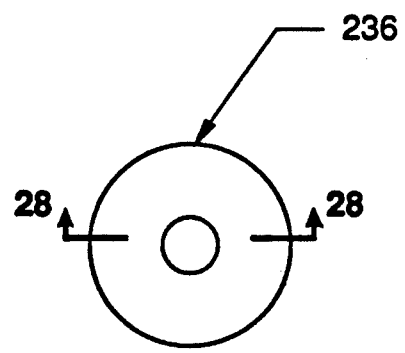
FIG. 27 is a proximal end view of the preferred embodiment of the diaphragm of the retractable syringe of FIG. 15.
Figure 29:
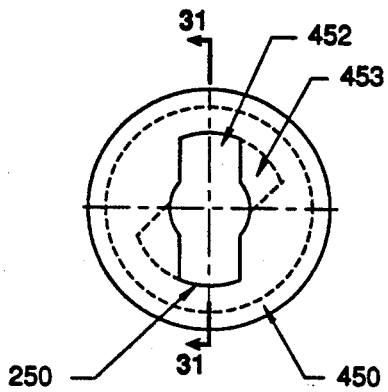
FIG. 29 is a distal end view of the preferred embodiment of the needle carrier of the retractable syringe of FIG. 15.
Figure 30:
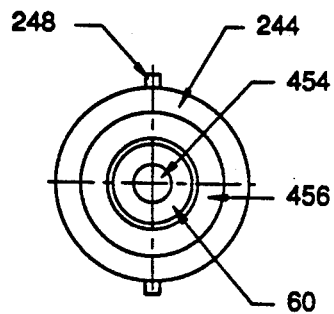
FIG. 30 is a proximal end view of the preferred embodiment of the needle carrier of the retractable syringe of FIG. 15.

Attached to the proximal end of retractor mechanism 421 there is mounted an injection piston 236 (FIGS. 27, 28), which is also disposed within barrel 212 when assembled. Injection piston 236 includes an entry port 442. Proximal to entry port 442 is an expandable, distortable (FIG. 43), mounting collar 444 that distorts so that port 442 abuts to the retractor pedestal 432 with the entry port 442 contacting the retractor pedestal 432 when assembled after the stinger latch 238 has passed through entry port 442 to disengage needle carrier 216 from mounting collar 214 as discussed below (FIG. 43). At the proximal end of mounting collar 444 is located the leading edge or proximal end 446 of injection piston 236 which includes an outer thick membrane portion 448 and an interior thin membrane portion 450, forming an interior detent 452 because of the differences in thickness. Detent 452 is sized to receive stinger latch 238 therein. Injection piston 236 is typically made of the same materials as set out above, having a rubber durometer of forty. Thus membrane 450 is expandable as impinged upon by stinger latch 238 and should not rupture under the action described below. Thus injection piston 236 maintains a liquid seal between the plunger 230 and the interior wall of barrel 212 during all stages of motion of the plunger 230 within the barrel 212.

Plunger 230 and barrel 212 may be made of a relatively hard material such as, for example, high density polypropylene or other suitable synthetic material. Barrel 212 may also be made of a relatively resilient material such as polyethylene or polypropylene, for example. The same material used for barrel 212 may also be employed for protective cover or sheath 418, 420, 422. All materials should be of a grade and quality suitable for human medical applications.

Piston 236 is usually of slightly larger diameter than the inside diameter of barrel 212 so that in service, the barrel telescopically receives the piston 236 as the piston traverses the barrel with the piston 236 deforming to stay in sealing relationship therewith. Piston 236 is sized and shaped to serve as a liquid or fluid displacement means within barrel 212 for withdrawing a liquid or fluid substance from another container, for example, and subsequently injecting the substance through needle 220 into a subject being treated. Of course, syringe 400 may be used for withdrawing liquid or fluid substances from a subject for subsequent testing, or for other purposes. In short, the retractable syringe 400 of the present invention may be used in any clinical setting, under any medical conditions.

Referring now to FIGS. 29-34, 42 and 43, needle carrier 216 is mounted within mounting collar 214 of barrel 212 from within the barrel, and needle cartridge 218 is subsequently mounted to the proximal end of needle carrier 216 from outside barrel 212. Needle carrier 216 has a generally circular conical main body 240 with a slight taper from its distal end 242 to its proximal end 244 to be contained in mounting collar 214 which is similarly tapered. A radially outwardly extending circumferential flange 246 is disposed around body 240 at its distal end 242. The distal surface 450 of flange 246 is slanted toward its center to facilitate insertion of the piston 236 therein and to continue the fluid path past surface 452 to channel 454. A plurality of radially outwardly extending bayonet lugs 248 are disposed on the exterior side wall of body 240 between flange 246 and proximal end 244. Preferably, there are two such lugs 248 which are diametrically opposed from one another. A latch recess 250 extends into body 240 of needle carrier 216 from its distal end 242. Latch recess 250 is shaped correlatively to stinger latch 238, as is more fully set out below.

A substantially annular blind bore or pocket 451, comprising a needle cartridge receiving pocket, extends longitudinally part way, preferably about half way, through main body 240 from its proximal end 244. In the center of pocket 451 there is disposed a needle cartridge support member 54, which may be integral, for example, with main body 240. Needle cartridge support member 54 extends from the distal end wall 456 of pocket 451 beyond the plane of the proximal end face 244 of main body 240, such that a substantial proximal end portion of member 54 protrudes out of the main body 240. As discussed above, needle cartridge support member 54 is substantially circular conical in configuration, and tapers slightly from its distal end at end wall 456 to its proximal end 60. This provides a pressure friction fit to receive the interior of needle cartridge 218. Needle cartridge support member 54 has a longitudinally extending central axial bore 62 therein, in fluid communication with latch recess 250 by channel 454.

Figure 31:
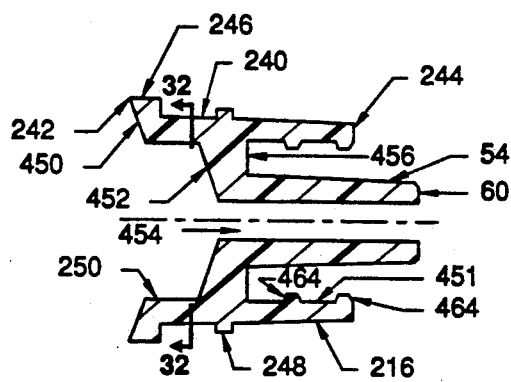
FIG. 31 is a longitudinal cross-section of the needle carrier of FIG. 29 taken along section lines 31—31 of FIG. 29.
Figure 32:
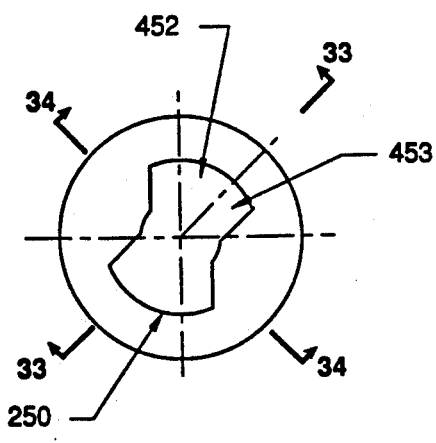
FIG. 32 is a cross-sectional view taken along section lines 32—32 of FIG. 31.
Figures 33, 34:
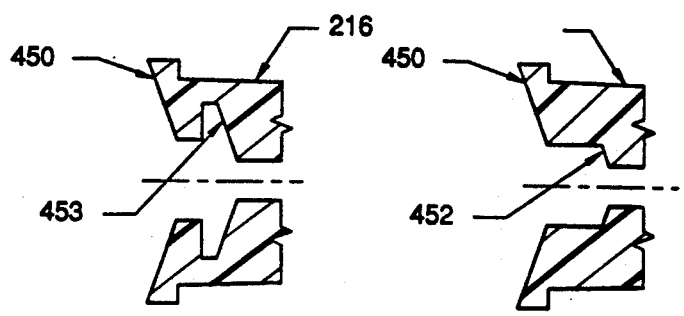
FIG. 33 is a partial longitudinal cross-sectional view of the needle carrier taken along section lines 33—33 of FIG. 32.
FIG. 34 is a partial longitudinal cross-sectional view of the needle carrier taken along section lines 34—34 of FIG. 32.

Pocket 451 has a pair of relatively steeply pitched, raised, that is, radially inwardly projecting, axially spaced apart ribs 464 around its outer wall, forming a pair of lands upon which a corresponding pair of tabs disposed on the distal end of the needle cartridge 218 ride in removing or installing the needle cartridge, as is more fully set out below. The ribs 464 begin, or intersect, the proximal end face of main body 240, on diametrically opposed sides thereof as is best shown in FIG. 31. These ribs form what is commonly referred to as a lure lock thread.

Mounting collar 214 includes a hub portion 428 extending from the proximal end 470 thereof to a relatively thick-walled needle carrier retaining portion 472 of barrel 212, forming an annular shoulder 474 therebetween. The hub portion 428 and needle carrier retaining portion 472 of barrel 212 have a substantially circular conical bore 476 therethrough, shaped correlatively to the outer profile of main body 240 of needle carrier 216. Between the upper or distal end of bore 276 in needle carrier retaining portion 472 and the interior wall 478 of barrel 212 against which piston 236 is sealingly engaged, is disposed a circular counterbore 480. Flange 246 of needle carrier 216 is received in counterbore 480 when the needle carrier 216 is locked in place in mounting collar 214. Flange 246 is somewhat resilient, so that it will sealingly engage counterbore 480 when carrier 216 is locked into place in collar 214.

Mounting collar 214 has a pair of diametrically opposed, substantially longitudinally extending slots 482 in the wall of bore 476, extending in a proximal direction from the interface between bore 476 and counterbore 480. Slots 482 intersect and communicate with a pair of inclined recesses or threads 484 in the wall of bore 476 which extend part way, for example 90° or less, around the inside wall of bore 476 and are inclined toward the proximal end 470 of hub portion 428. Threads 484 as shown are right-hand threads, but left-hand threads could be used, as desired. Threads 484, unlike the embodiment of FIG. 11 even though the mounting collar 214 is the same numbered item in both, does not have a friction rise or bump on their proximal surfaces near their blind ends. Slots 482 are adapted to receive bayonet lugs 248 on needle carrier 216, and when the needle carrier is so inserted into collar 214 and rotated in the proper direction, preferably 90° or less, lugs 248 traverse the buttresses of threads 484 until they bottom out at the blind ends of the threads. Due to the inclined nature of threads 484, rotation of the needle carrier to the right (for a right-hand thread 484) will tend to draw the needle carrier 216 more tightly into the mounting collar 214, and will tend to energize the seal between flange 246 and counterbore 480.

Unlike the embodiment of FIG. 11, no additional force is required to pass the lugs 248 along threads 484 for there are no friction rises or bumps in either direction. Accordingly, when the lugs 248 are fully seated in the blind ends of threads 484, they are bounded only on one side by the blind end walls of the threads 484, but the lugs 248 will still be relatively securely seated in the blind ends of threads 484, and the needle carrier 216 will in turn be relatively securely latched into the mounting collar 214. Bumps are not necessary, however, because sufficient frictional forces exist between needle carrier 216 and mounting collar 214 to prevent relative rotation between them during installation and/or removal of a needle cartridge as discussed further below.

FIG. 42 illustrates the needle carrier 216 fully seated and latched into collar 214. Such installation and latching occurs within barrel 212 as the syringe 400 is being assembled prior to use. FIG. 42 shows the needle carrier 216 in the same position depicted in FIG. 3, but the mounting collar 214 has been rotated, preferably, as stated above, 90° or less. It should be understood that a retaining pin, and corresponding bores, may not be necessary because sufficient frictional forces exist between needle carrier 216 and mounting collar 214 to prevent relative rotation of such members during installation and/or removal of a needle cartridge.

Mounting collar 214 further includes a circumferentially extending extension groove 498 around the periphery of hub portion 428 (unlike groove 298 in the other like numbered collar 214 of FIG. 11) and adapted to receive a correlatively shaped ridge or land 500 disposed on locking safety cover 423, or alternatively 418, 420, 422, as more fully described hereinafter.

Referring now particularly to FIGS. 10, 42 and 43, the needle cartridge 218 of the present invention is shown in more detail. Needle cartridge 218 includes an elongate, generally conical, hollow main body 502 which tapers slightly from its upper or distal end 504 to its lower or proximal end 506. Main body 502 of needle cartridge 218 has a tapered, longitudinally extending, central axial bore 508 which has a taper substantially the same as the taper of the outside surface of needle cartridge support member 54, so as to form a close fit therewith when installed on syringe 400. Bore 508 is in fluid communication with bore 454 in needle cartridge support member 54. Needle cartridge 218 may also include a substantially circular cylindrical extension portion extending in a proximal direction from proximal end 506 of main body 502 as in the other embodiments. A plurality of substantially longitudinally extending stiffening ribs may be disposed on main body 502 and the extension portion along their outer sides. If this is so, there would be preferably four (4) such ribs disposed at substantially 90° to one another. If there is a cylindrical extension of needle cartridge 218 it would have a central axial bore therethrough, which is in fluid communication with bore 508 of main body 502. A hypodermic needle 220 of selected size and shape is mounted within the central axial bore and if there is a cylindrical extension, in the cylindrical extension. Needle 220 has a longitudinally extending bore therethrough of selected diameter, which bore is in fluid communication with bore 508 and, hence, bore 454 in needle cartridge support member 54.

The upper or distal end 504 of needle cartridge 218 includes a pair of diametrically opposed, outwardly extending tabs or ears 514 (FIG. 42). When the distal end 504 of needle cartridge 218 is inserted longitudinally axially into needle carrier 216 from the proximal end thereof and rotated to the right (for a right-hand thread 464 to the left for a left-hand thread), each of tabs 514 engages and travels along one of the helical threads 464, which draws needle cartridge 218 onto needle cartridge support member 54 and forces the needle cartridge into secure, stable, sealed relationship with the needle cartridge support member. The tight frictional engagement of tabs 514 against the walls of pocket 52 provides additional lateral stability and support for needle cartridge 218 when mounted in needle carrier 216. In order to remove needle cartridge 218 from needle carrier 216, for example, to replace it with a different shaped or sized needle, as desired, the needle cartridge is rotated to the left (for a right-hand thread 464; to the right for a left-hand thread), and tabs 514 travel along threads 464 until they are released therefrom at or near proximal end 244 of main body 240. It should be understood, however, that depending upon whether threads 464, 484 are right-hand, left-hand or one of each, either the removal of needle cartridge 218 onto needle carrier 216, will tend to rotate the members 214, 216 with respect to one another in a direction so as to further engage lugs 248 into threads 484.

Referring now particularly to FIGS. 23, 25 and 26, stinger latch 238 of plunger 230 has a main body 239 of generally conical configuration with a retaining lip 516 around its upper periphery. Stinger latch 238 also includes a pair of rotational lugs 518 extending longitudinally axially from below lip 516 to the proximal end or apex of main body 239. Rotational lugs 518 are disposed on diametrically opposed sides of stinger latch 238. Stinger latch 38 is adapted to stretch an inner shoulder 442 of the resilient flange or piston 236 and to descend into recess 250 formed in the distal end of needle carrier 216 when plunger 230 is advanced to the proximal end of its stroke. Stinger latch 238 is thus stabbed into engagement with a tapered latch seat 452 in recess 250. Recess 250 has correlatively shaped groove 453 extending longitudinally axially on opposite sides of latch seat 452 for receiving rotational lugs 518. When stinger latch 238 is pushed into the recess 250 of needle carrier 216 in substantially random angular orientation with respect thereto, latch 238 may be rotated slightly one way or the other in order to bring lugs 518 into engagement with latch seat 452 and thus grooves 453 of recess 250. When lugs 518 have so engaged grooves 453, further rotation of plunger member 230 will rotate piston 436, stinger latch 238, needle carrier 216, needle cartridge 218, and needle 220.

Rotation of the plunger member 230 and injection piston 436 in the appropriate direction which rotates the needle carrier 216 and its lugs 248 along the threads 484 until the lugs are in alignment with slots 482, whereupon withdrawal of the plunger 230 back into the barrel 212 also withdraws the needle carrier 216, needle cartridge 218, and needle 220 as a unit back into the barrel 212, eliminating the possibility of a needle stick injury.

The upper or distal end of barrel 212 has an annular area or land 530 of reduced inside diameter and with sloping distal end 531 and vertical proximal end 533. An annular latching groove 532 is formed at the proximal end of land 530, adjacent to an annular latching rib 534 disposed proximally of latching groove 532. The latching groove 532 is of about the same inside diameter as the inner diameter of barrel 212 below land 530. Like land 530, the annular latching rib 534 has an inside diameter smaller than the inside diameter of barrel 212 below land 530; the inside diameter of rib 534 may, for example, be smaller than land 50. When plunger 230 is withdrawn into barrel 212 in order to retract needle 220 into the barrel, and as the piston 236 is pulled against the rib 534, the rib wall is slanted to permit the rounded edge of the piston 236 to pass over it into seated position in latching groove 532. Since the thickness of rib 534 is greater than that of the wall of barrel 212 below the rib, considerably greater force is required to force the rib outwardly. Accordingly, somewhat greater force is required to pull the piston 236 over the rib 534 than is required to withdraw the plunger 230 through the barrel. Once seated in latching groove 532, piston 236 is substantially resistant to movement in either direction. Although it is preferred to provide rib 534 and groove 532 to hold piston 236 in retracted position within barrel 212, the rib and groove may be omitted, and the frictional force to overcome the surface 533 may be relied upon instead to hold the piston in place. Further, all of the rib, groove, and land may be omitted, because with the breaking off of the plunger 230, infra, the friction of the barrel against the piston 236 may be sufficient to latch the needle in retracted position in the barrel.

Plunger member 23 is provided with shear indent 440 in ribs 232 at a location such as to be substantially flush with the distal end of barrel 212 when piston 236 is seated in groove 532. Lateral force may then be applied to the distal end of plunger 230 to break off the plunger at the shear indent 440, leaving the remainder of the plunger disposed inside barrel 212 with its distal end substantially flush with the distal end of the barrel 212.

Figure 35:
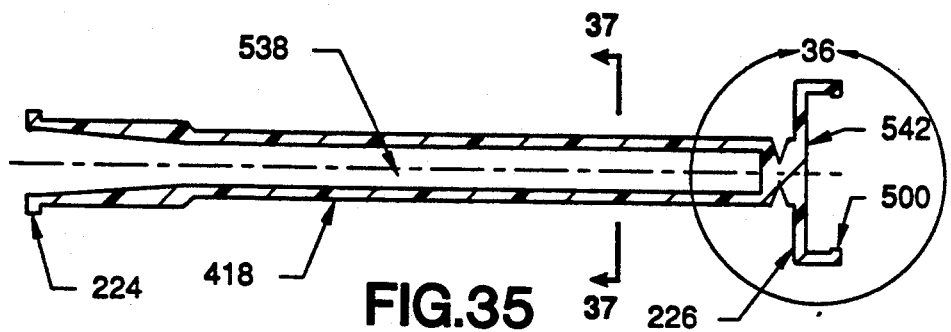
FIG. 35 is a longitudinal cross-sectional view of one option of the alternate embodiments of the cap of the preferred embodiment of the retractable syringe of FIG. 15.
Figure 38:
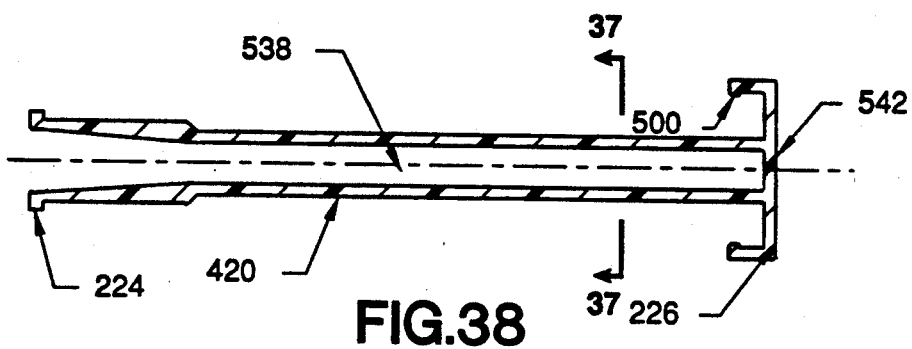
FIG. 38 is a longitudinal cross-sectional view of a second alternative embodiment option of the cap of the preferred embodiment of the retractable syringe of FIG. 15.
Figure 39:
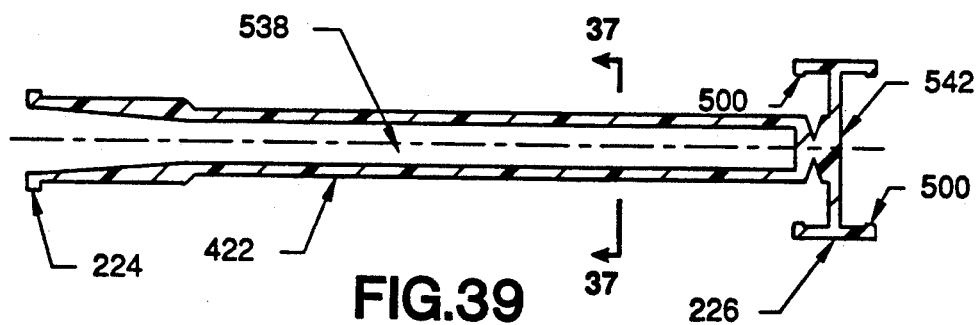
FIG. 39 is a longitudinal cross-sectional view of a third alternative embodiment option of the cap of the preferred embodiment of the retractable syringe of FIG. 15.
Figure 37:
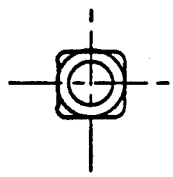
FIG. 37 is a cross-sectional view of FIG. 35 taken along section lines 37—37 of FIGS. 35, 38 or 39.
Figure 36:
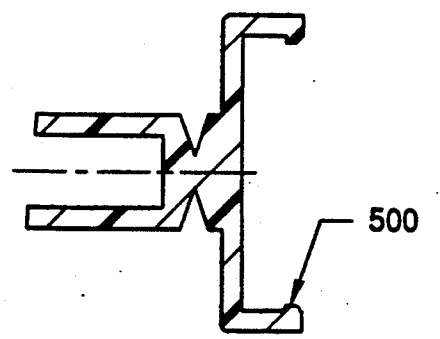
FIG. 36 is a detail view of the proximal end of the cap of FIG. 35.

The syringe 400 is delivered to the person who will use it either in the assembled configuration shown in FIG. 42, or in a similar to the configuration shown in FIG. 42. The operator may proceed to use it as is, or he or she may choose to remove the needle cartridge and needle supplied with the particular syringe and replace it with another needle cartridge and needle. Such a situation might arise, for example, if the operator wishes to use a needle of a different shape, such as longer or shorter, or of a different size, such as with a larger or smaller diameter and/or bore. If the operator wishes to replace the needle cartridge and needle, he or she grasps the needle cartridge firmly around the main body 502 and rotates it in the appropriate direction to unscrew the cartridge 218 from the needle carrier pocket 451. Preferably, during this removal and replacement procedure a locking safety cover such as alternative embodiments 419, 420, 422 or the carrier supplied with the needle cartridges 218 remains on the needle cartridge being removed and on the needle cartridge being installed in its place. locking safety covers at this stage of the procedure will have their longer ends 24 frictionally retained around the proximal ends of main bodies 502 of needle cartridges 218, with needles 220 being safely received in tapered blind bores 538 of the covers (FIGS. 35, 38, 39). After removing he supplied needle cartridge, the operator then installs the desired needle cartridge by grasping it firmly, preferably with its cover in place, inserting its distal end into pocket 451, nd rotating it in the appropriate direction to screw it securely into place as shown, for example, in FIG. 42, so that it is integral.

Figure 44:
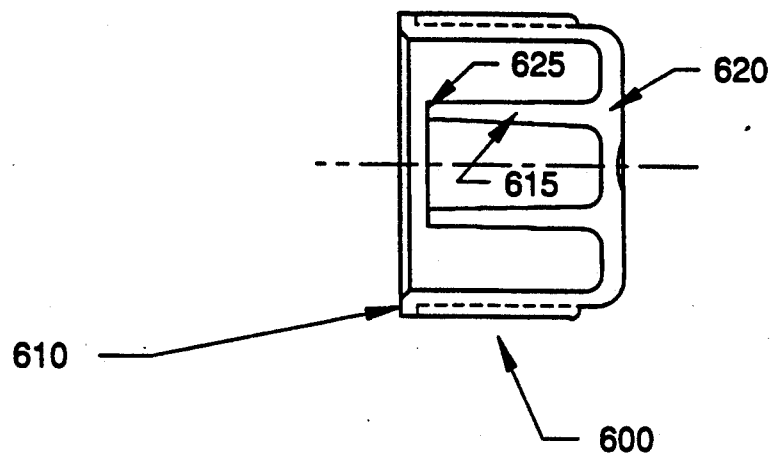
FIG. 44 is a longitudinal cross-sectional view of an alternate embodiment of the cap of the retractable syringe of FIG. 15.

Should the operator wish to prefill the barrel with a dosage and thus no needle cartridge is initially provided, an alternate cap 60 may be used (FIG. 44). Such a cap has flanges 610 corresponding to the lure lock thread formed by ribs 464. An internal cylindrical body 615 extends from end 620 and is dimensionsed to extend such that as the flanges 610 move into the lure lock thread of ribs 464, the end 625 of body 615 sealingly abuts the end 60 of member 54.

Figure 40:
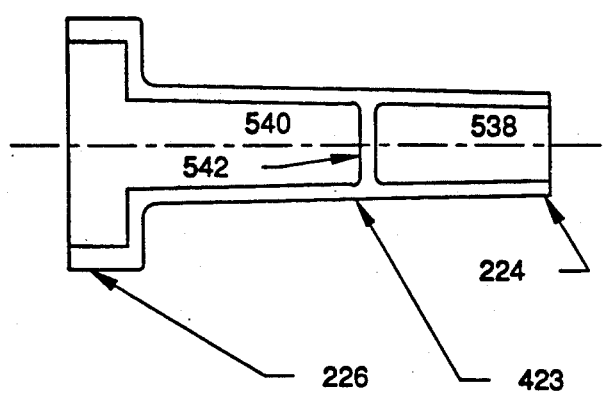
FIG. 40 is a longitudinal cross-sectional view of the preferred embodiment of the cap of the retractable syringe of FIG. 15.
Figure 41:
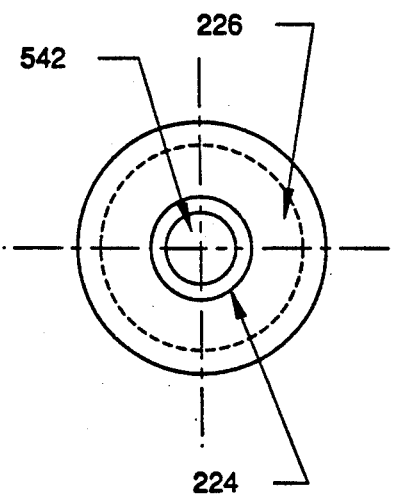
FIG. 41 is an end view of the preferred embodiment of the cap of the retractable syringe of FIG. 15.

If the syringe 400 were to be supplied with no needle cartridge 218 installed thereon, as is preferable, the operator simply has to install a desired needle cartridge as set out above so that it is integral. In order to ensure that a syringe 400 supplied without a needle cartridge is not contaminated prior to the time a needle cartridge is installed, it is preferred that a locking safety cover 423 be installed on the hub 428 of the mounting collar 214, as shown, for example, in FIG. 40, when the syringe 400 is manufactured so a to protectively enclose the barrel. For this purpose the larger end 226 of cover 423 is provided with an axially extending blind bore 540 of a shape correlative to that of hub 428 and a diameter slightly smaller than the outside diameter of the hub, so that when the cover is forced over the hub, the cover will stretch slightly and sealingly engage the hub. As shown in the alternate embodiments of FIGS. 35, 38 and 39, annular locking ridge or land 500 of cover 418, 420, 422 will engage and seat in annular groove formed on the distal side of protrusion 498 around hub 428 in order to positively retain cover 418, 420, 422 on hub 428. Otherwise friction as in the preferred embodiment of FIG. 40 will hold the cover 423 on hub 428. A fluid barrier 542 between blind bore 540 and bore 538 of any of the covers prevents fluid communication between the bores.

When the desired needle cartridge is fully installed and in place in needle carrier 216, syringe 400 is ready for use. Piston 436 is free to be moved by plunger 230 from below rib 534 to a position just short of latching engagement between stinger latch 238 and needle carrier 216. The operator may then remove the needle cover from needle cartridge 218 and needle 220, and proceed to either draw a liquid or fluid substance from a container through needle 220 into barrel 212 and inject it into a subject, or insert the needle 220 into a subject with barrel 212 empty and withdraw blood or other fluids from the subject for depositing into a container for testing or the like. As discussed above, if the barrel 212 is prefilled, when the needle carrier 216 is attached, syringe 400 is ready for use.

After the syringe 400 has been used, plunger member 230 is pushed firmly in a proximal direction until stinger 238 is forced into recess 450 in needle carrier 216, and the plunger is rotated slightly one way or the other, if necessary, so that lugs 518 of stinger 238 seat in grooves 524 of recess 450. Engagement of stinger 238 in recess 450 is shown, for example, in FIG. 43. The plunger 30 is then rotated in the appropriate direction to move lugs 248 along threads 484 into register with slots 482.

The plunger head 434 is then pulled in a distal direction to pull needle carrier 216, needle cartridge 218, and needle 220 into barrel 212 until piston 236 travels over rib 534 and seats in groove 532. When or not groove 532 is used, the distal portion of the plunger member 230 is broken off at shear indent 440 and discarded, leaving the broken end of the plunger substantially flush with the end of the barrel and if groove 532 is used, the remainder of the plunger securely latched within the barrel 212. The needle cartridge 218 and needle 220 are thus securely retained and immobilized in protective isolation within the barrel, as shown in FIG. 43. The protective cover 423 may then be installed on the hub 428 of collar 214 in order to prevent excess fluids or residue remaining in the syringe 400 from leaking out of the syringe. The used syringe may then be safely discarded without further danger of a needle stick injury.

Figure 45:
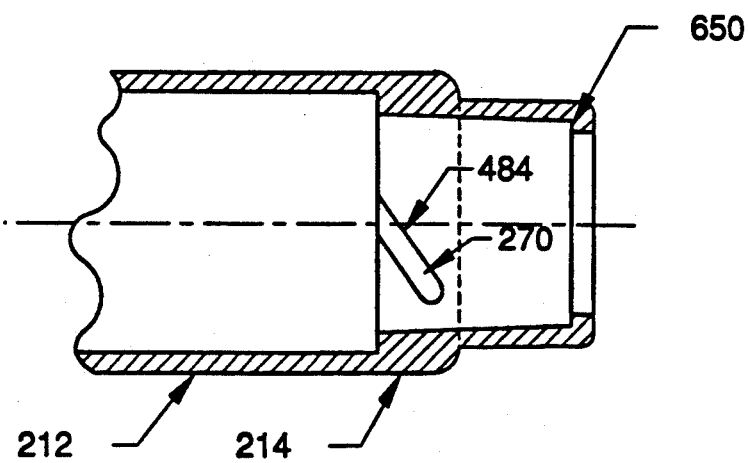
FIG. 45 is a longitudinal cross-sectional view of another preferred embodiment of the barrel of the retractable syringe of FIG. 15.

As best seen in FIG. 45, threads 484 do not require slots 482. Friction bump 270 is supplied in thread 484. In addition, a lip 650 is located at the proximal end of mounting collar 214. This will further restrain the proximal end of needle holder 216 as lugs 248 are inserted in threads 484.

Figure 46:
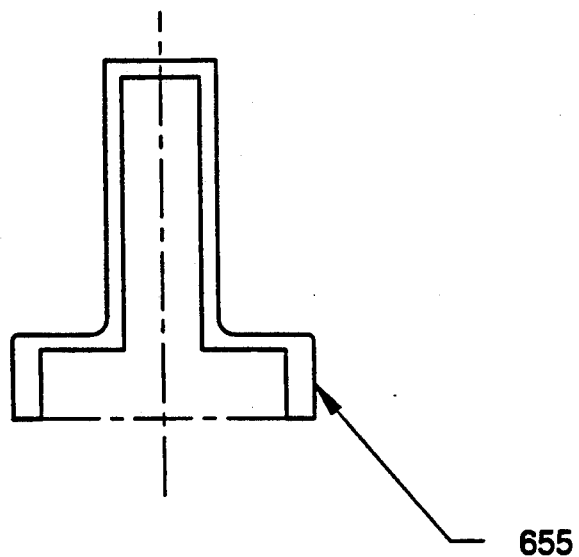
FIG. 46 is a longitudinal cross-sectional view of another preferred cap of the preferred embodiment of the retractable syringe of FIG. 15.

As seen in FIG. 46, another embodiment of the cap 656 is shown. This cap is similar to the cap of FIG. 40, except it does not have the end 224.

Figure 47:
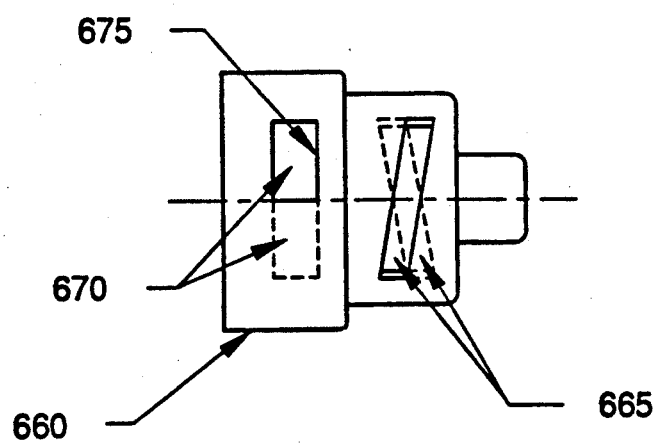
FIG. 47 is a longitudinal cross-sectional view of a preferred embodiment of the needle holder of the retractable syringe of FIG. 15.
Figure 48A:
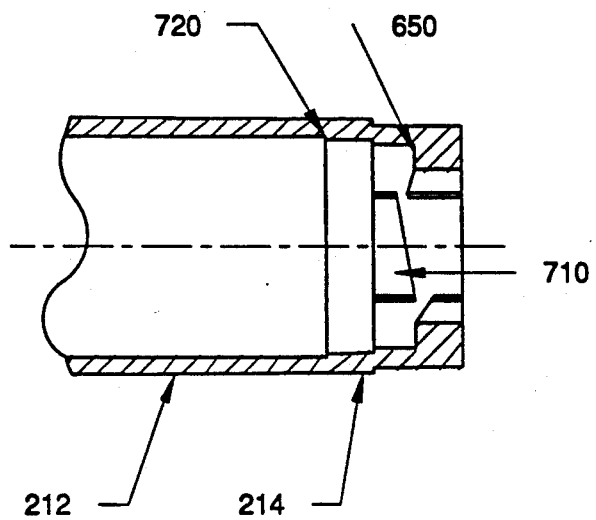
FIG. 48A and 48B is a longitudinal cross-sectional view of the preferred embodiment of the barrel of the preferred embodiment of the retractable boll syringe of FIG. 15 corresponding to the needle holder of FIG. 47.
Figure 48B:
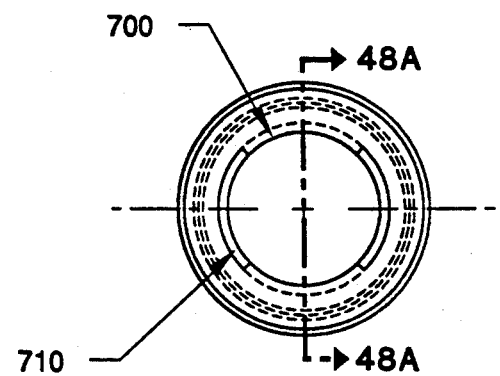

As shown in FIG. 47, needle holder 660 is substantially identical to the needle holder 216, except for certain lugs as discussed below. Instead of lugs 248 as shown in FIG. 31, needle holder 660 is supplied with incline threads 665 and with extensions 670 on the same portion of needle holder 660 as threads 665. Extensions 670 have shoulders 675. Corresponding to needle holder 660, a modified mounting collar 214 as shown in FIG. 48. Mounting collar 214 is shown in FIG. 48. Mounting collar 214 as shown in FIG. 48 includes slots 700 on opposite sides of mounting collar 214, and bottom threads 710 disposed at a 90° angle laterally around mounting collar 214. In addition, shoulder 720 is provided in the interior of barrel 212 spaced apart approximately the distance that should 675 is spaced apart from threads 665. Thus as threads 665 are inserted into slots 700 and needle holder 660 is rotated, threads 665 ride up threads 710 in frictional engagement until shoulders 675 engaged shoulder 720. Lip 650 supplies additional containment, thereby making a secure engagement of the threads 665, 710.

Figure 49A:
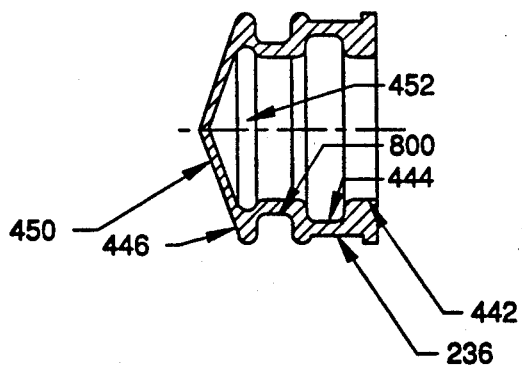
FIG. 49A and 49B is a longitudinal cross-sectional view of a preferred embodiment of the piston of the retractable syringe of FIG. 15.
Figure 49B:
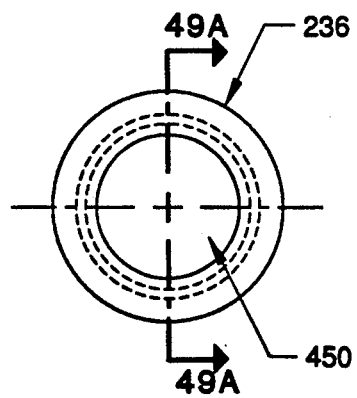

As shown in FIG. 49, a modified piston or seal 236 has an elongated indent 800, as well as section 450 being more elongated, eliminated section 448. This permits rotation of section 450 opposite to that of the piston 236 shown in FIG. 28, which only has an internal indentation 444.

While preferred and alternative embodiments of the invention have been shown and described, many modifications thereof may be made by those skilled in the art without departing from the spirit of the invention. Therefore, the scope of the invention should be determined in accordance with the following claims.

What is claimed is:

1. A retractable syringe for use with a hypodermic needle cartridge [18, 218], comprising:
   a barrel [12, 212] having a proximal end and a distal end, said proximal end of said barrel including a mounting collar [14, 214] with a bore [76] having a wall;
   a piston plunger [30, 230], having sealing means [36, 236] telescopingly received within said distal end of said barrel [12, 218];
   a needle carrier [660] having a body, said body having a proximal end and a distal end and an exterior wall;

means [48, 248] disposed on said body and engageable in contact with correlatively shaped means [84, 256] disposed on said mounting collar [14, 214] for releasably latching said body in said bore of said mounting collar [14, 214], said distal end of said body having means [50, 250] engageable with said sealing means [36, 236] for retracting said body into said barrel [12, 212]; and wherein the end [446] of said sealing means [236] rotates upon intrusion of said plunger [30, 230] and side [800] collapses.

2. The retractable syringe of claim 1, wherein said rotation is exterior rotation.

3. The retractable syringe of claim 1, wherein said sealing means [236] includes a thin upper surface [450] and an exterior cavity [452] and an interior detent [444] and an exterior detent [800].

4. A retractable syringe for use with a hypodermic needle cartridge [18, 218], comprising:
- a barrel [12, 212] having a proximal end and a distal end, said proximal end of said barrel including a mounting collar [14, 214] with a bore [76] having a wall;
- a piston plunger [30, 230], having sealing means [36, 236] telescopingly received within said distal end of barrel [12, 218];
- a needle carrier [660] having a body, said body having a proximal end and a distal end and an exterior wall;
- engagement means [665, 670] disposed on said body and engageable in contact with correlatively shaped means [700, 710, 720] disposed on said mounting collar [14, 214] for releasably latching said body in said bore of said mounting collar [14, 214], said distal end of said body having means [50, 250] engageable with said sealing means [36, 236] for retracting said body into said barrel [12, 212]; and wherein the engagement means [665, 670] are frictionally held in engagement with said shaped means [700, 710, 720] at two longitudinally separated positions.

5. The retractable syringe of claim 4, wherein said engagement means [665, 670] includes included threads [665] and shoulders [675] formed on extensions [670] of said engagement means [665, 670], said shaped means [700, 710, 720] includes slots [700] sized to admit threads [665], bottom threads [710] engageable with said threads [665] and bottom shoulders [720] engageable with said shoulders [675].

6. The retractable syringe of claim 5, wherein said slots [700] are spaced laterally around collar [214].

7. The retractable syringe of claim 5, wherein said shoulders [720] are located in said barrel [12, 212].

8. The retractable syringe of claim 5, wherein there is further included a lip [650] juxtaposed with said bottom threads [710] having means for containing said threads [66].

* * * * *